(12) United States Patent
Matzger et al.

(10) Patent No.: US 9,132,411 B2
(45) Date of Patent: Sep. 15, 2015

(54) STRATEGIES, LINKERS AND COORDINATION POLYMERS FOR HIGH-PERFORMANCE SORBENTS

(71) Applicant: The Regents of the University of Michigan, Ann Arbor, MI (US)

(72) Inventors: Adam J. Matzger, Ann Arbor, MI (US); Antek G. Wong-Foy, Ann Arbor, MI (US); Oliver Lebel, Kingston (CA)

(73) Assignee: The Regents of the University of Michigan, Ann Arbor, MI (US)

( * ) Notice: Subject to any disclaimer, the term of this patent is extended or adjusted under 35 U.S.C. 154(b) by 124 days.

(21) Appl. No.: 13/775,561

(22) Filed: Feb. 25, 2013

(65) Prior Publication Data

US 2013/0237411 A1 Sep. 12, 2013

Related U.S. Application Data

(63) Continuation-in-part of application No. 11/848,219, filed on Aug. 30, 2007, now Pat. No. 8,383,545.

(51) Int. Cl.

| | |
|---|---|
| *C07C 69/76* | (2006.01) |
| *C07F 1/00* | (2006.01) |
| *B01J 20/22* | (2006.01) |
| *C07C 69/78* | (2006.01) |
| *B01D 53/02* | (2006.01) |
| *C07C 63/331* | (2006.01) |
| *B01J 31/16* | (2006.01) |

(52) U.S. Cl.
CPC .............. *B01J 20/226* (2013.01); *B01D 53/02* (2013.01); *B01J 31/1691* (2013.01); *C07C 63/331* (2013.01); *C07C 69/78* (2013.01); *B01D 2253/202* (2012.01); *B01D 2257/108* (2013.01); *B01D 2257/504* (2013.01); *B01J 2531/0219* (2013.01); *Y02C 10/08* (2013.01)

(58) Field of Classification Search
CPC ............................. B01J 20/226; C07C 69/78
USPC .............................. 502/401; 560/85; 556/115
See application file for complete search history.

(56) References Cited

U.S. PATENT DOCUMENTS

| | | | |
|---|---|---|---|
| 3,666,709 A | 5/1972 | Suzuki et al. | |
| 5,648,508 A | 7/1997 | Yaghi | |
| 6,617,467 B1 | 9/2003 | Mueller et al. | |
| 6,624,318 B1 | 9/2003 | Mueller et al. | |
| 6,893,564 B2 | 5/2005 | Mueller et al. | |
| 6,929,679 B2 | 8/2005 | Mueller et al. | |
| 6,930,193 B2 | 8/2005 | Yaghi et al. | |
| 7,008,607 B2 | 3/2006 | Mueller et al. | |
| 7,179,765 B2 | 2/2007 | Mueller et al. | |
| 7,196,210 B2 | 3/2007 | Yaghi et al. | |
| 7,202,385 B2 | 4/2007 | Mueller et al. | |
| 7,279,517 B2 | 10/2007 | Mueller et al. | |
| 7,309,380 B2 | 12/2007 | Meuller et al. | |
| 7,343,747 B2 | 3/2008 | Mueller et al. | |
| 7,411,081 B2 | 8/2008 | Mueller et al. | |
| 2003/0004364 A1 | 1/2003 | Yaghi et al. | |
| 2003/0078311 A1 | 4/2003 | Mueller et al. | |
| 2003/0148165 A1 | 8/2003 | Mueller et al. | |
| 2003/0222023 A1 | 12/2003 | Mueller et al. | |
| 2004/0081611 A1 | 4/2004 | Mueller et al. | |
| 2004/0225134 A1 | 11/2004 | Yaghi et al. | |
| 2004/0249189 A1 | 12/2004 | Mueller et al. | |
| 2004/0265670 A1 | 12/2004 | Mueller et al. | |
| 2005/0004404 A1 | 1/2005 | Mueller et al. | |
| 2005/0124819 A1 | 6/2005 | Yaghi et al. | |
| 2005/0154222 A1 | 7/2005 | Mueller et al. | |
| 2005/0192175 A1 | 9/2005 | Yaghi et al. | |
| 2006/0035095 A1 | 2/2006 | Calundann et al. | |
| 2006/0057057 A1 | 3/2006 | Mueller et al. | |
| 2006/0135824 A1 | 6/2006 | Mueller et al. | |
| 2006/0154807 A1 | 7/2006 | Yaghi et al. | |
| 2006/0185388 A1 | 8/2006 | Mueller et al. | |
| 2006/0252641 A1 | 11/2006 | Yaghi et al. | |
| 2007/0068389 A1 | 3/2007 | Yaghi | |
| 2007/0202038 A1 | 8/2007 | Yaghi et al. | |

OTHER PUBLICATIONS

Seki et al., Chemistry Letters (2001), (4), 332-333.*
Shin-Ichiro Noro et al., "A New Methane Adsorbent, Porous Coordination Polymer", Angew. Chem. Int. Ed. 2000, 39, No. 12, pp. 2081-2084.
Danil N. Dybtsev, et al., "Rigid and Flexible: A Highly Porous metal-Organic Framework with Unusual Guest-Dependent Dynamic Behavior", Angew. Chem. Int. Ed. 2004, 43, pp. 5033-5036.
Danil N. Dybtsev, et al., "A Homochiral Metal-Organic Material with Permanent Porosity, Enantioselective Sorption Properties, and Catalytic Activity", Angew. Chem. Int. Ed. 2006, 45, pp. 916-920.
Ramanathan Vaidhyanathan, et al., "A Family of Nanoporous Materials Based on an Amino Acid Backbone", Angew. Chem. Int. Ed., 2006, 45, pp. 6495-6499.
Simon M. Humphrey, et al., "Porous Cobalt (II)—Organic Frameworks with Corrugated Walls: Structurally Robust Gas-Sorption Materials", Angew. Chem. Int. Ed. 2007, 46, 272-275.
Xin-Long Wang, et al., "An Unprecedented Eight-Connected Self-Penetrating Network basked on Pentanuclear Zinc Cluster Building Blocks", The Royal Society of Chemistry 2005, Chem. Commun., 2005, pp. 4789-4791.
Samadora Thushari et al., "Microporous Chiral metal Coordination Polymers: Hydrothermal Synthesis, Channel Engineering an dStability of Lanthanide Tartrates", The royal Society of Chemistry 2005, Chem. Commun., 2005, pp. 5515-5517.

(Continued)

*Primary Examiner* — Porfirio Nazario Gonzalez
*Assistant Examiner* — Kofi Adzamli
(74) *Attorney, Agent, or Firm* — Brooks Kushman P.C.

(57) ABSTRACT

A linking ligand compound includes three bidentate chemical moieties distributed about a central chemical moiety. Another linking ligand compound includes a bidentate linking ligand and a monodentate chemical moiety. Coordination polymers include a plurality of metal clusters linked together by residues of the linking ligand compounds.

16 Claims, 11 Drawing Sheets

(56) References Cited

OTHER PUBLICATIONS

Junhua Jia, et al., "Twelve-Connected Porous Metal—Organic Frameworks with High H2 Adsorption", The Royal Society of Chemistry 2007, Chem. Commun., 2007, pp. 840-842.

Wei Chen, et all., "Photoluminescent metal—Organic Polymer Constructed from Trimetallic Clusters and Mixed Carboxylates", Inorganic Chemistry, 2003, 42, pp. 944-946.

Partha Mahata, et al., "A New Series of Three-Dimensional Metal—Organic Framework, et al.", Inorganic Chemistry, 2007, 46, pp. 1250-1258.

Jung Soo Seo, et al., "A Homochiral Metal-Organic Porous Material for Enantioselective Separation and Catalysts", Nature, vol. 404, Apr. 27, 2000, pp. 982-986.

Grenier-Loustalot et al, Mechanisms and kinetics of polymerization of thermoplastic polyimides.II Study of bridged dianhydride/aroamtic amine systems, 1993, Journal of polymer Science, Part A: Polymer chemistry, 31(12), p. 3149-63.

Kim et al, Enantioselective catalysis of the triplex diels-alder reaction: a study of scope and mechanism, 1992, Journal of the American Chemical Society, 114(24), p. 9309-17.

Holy et al, Self-assembly of enantiopure and racemic 2,2', 6,6'-tetrasubsituted biaryl tectons into hydrogen bonded chiral squares and infite chiral square layers, 2001, Tetrahedron :Asymmetry, 12(21), p. 3035-3045.

Echigo et al, A polyimide precursor solution based on a novel concept, 1998,Journal of polymer Science, Part A: Polymer chemistry, 36(11), p. 1961-1964.

Csoeregh et al, Crystalline host-guest complexex involving carboxylic acid host and a dimethyl sulfoxide guest:x-ray crystal structures of two inclusion species, Journal of Inclusion Phenomena and Molecular Recognition in Chemistry, 1995, voulme date 1994-1995, 20(3), p. 253-266.

Plummer et al, Synthesis of chelating Bidentate and Tridentate Cyano Ligands and Their complexes with Group 7 Metal Carbonyls, Inorganic Chemistry, vol. 22, No. 24, 1983, p. 3492-3497.

\* cited by examiner

STRATEGIES, LINKERS AND COORDINATION POLYMERS FOR HIGH-PERFORMANCE SORBENTS

CROSS-REFERENCE TO RELATED APPLICATIONS

This application is a continuation-in-part of U.S. application Ser. No. 11/848,219 filed Aug. 30, 2007, now U.S. Pat. No. 8,383,545, issued Feb. 26, 2013, the disclosure of which is incorporated in its entirety by reference herein.

STATEMENT REGARDING FEDERALLY SPONSORED RESEARCH OR DEVELOPMENT

This invention was made with government support under DE-FC26-05NT42447 awarded by the Department of Energy. The Government has certain rights in the invention.

BACKGROUND OF THE INVENTION

1. Field of the Invention

In at least one aspect, the present invention relates to the synthesis of multidentate organic ligands, the use of these ligands is to form porous coordination polymers and their application as sorbents or catalyst components.

2. Background Art

Microporous materials are in high demand because of their ability to adsorb a wide variety of guest molecules. These sorption properties make microporous materials attractive for applications such as storage, separation or catalysis. Optimization of these applications requires a combination of high surface area, tunable functionality, and defined pore structure.

Among different classes of microporous materials, coordination polymers have demonstrated a high efficiency for the uptake of several gases and organic molecules. The periodicity of such systems and the ability to modulate the pore size and surface area through modification of either the organic linker or metal cluster have made coordination polymers extremely appealing for sorption and storage applications. A few benchmark coordination polymers which are developed for these purposes include MOF-5 and HKUST-1.

Although the prior art microporous materials work reasonably well, there are a number of unsolved concerns. For example, many materials have relatively low surface areas and pore volumes, with broad pore size distributions.

Against this prior art background, there is still a desire for novel multidentate ligands that are useful for constructing porous materials.

SUMMARY OF THE INVENTION

The present invention solves one or more problems of the prior art by providing a compound that is useful as a linking ligand or a precursor to a linking ligand for forming porous materials. The compound of this embodiment is described by Formula I:

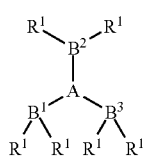

wherein:
$R^1$ is $CO_2R^2$, $CONR^2_2$, CN, $C_{2-8}$ alkynyl, or $C_{4-18}$ heteroatom-containing aromatic ring system;
$R^2$ is H, a metal cation, an organic cation, a $C_{1-8}$ alkyl, a $C_{6-18}$ aromatic ring system, or a $C_{4-18}$ heteroatom-containing aromatic ring system;
A is a $C_{6-18}$ aromatic ring system or $C_{4-18}$ heteroatom-containing aromatic ring system;
$B^1$, $B^2$, $B^3$ are each independently a $C_{6-18}$ aromatic ring system, a $C_{6-18}$ heteroatom-containing ring system, $C_{7-18}$ alkyl aryl, or $C_{5-18}$ alkyl heteroaryl. In another variation, $B^1$, $B^2$, $B^3$ are the same.

In another embodiment of the present invention, another compound that is useful as a linking ligand or a precursor to a linking ligand for forming porous materials is provided. The compound of this embodiment is described by Formula II:

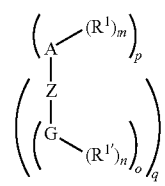

wherein:
$R^1$ and $R^{1'}$ are each independently $CO_2R^2$, $CONR^2_2$, CN, $C_{3-8}$ alkynyl, or a $C_{4-18}$ heteroatom-containing aromatic ring system;
$R^2$ is H, a metal cation, an organic cation, $C_{1-8}$ alkyl, an aromatic ring system, or a $C_{4-18}$ heteroatom-containing aromatic ring system;
A and G are each independently a $C_{6-18}$ aromatic ring system or a $C_{4-18}$ heteroatom-containing aromatic ring system;
Z is absent or a $C_{6-18}$ aromatic ring system or a $C_{4-18}$ heteroatom-containing aromatic ring system, $C_{7-18}$ alkyl aryl, heteroaryl, $C_{1-8}$ alkyl, $C_{2-8}$ alkenyl, or $C_{2-8}$ alkynyl; and
m, n, o, p and q are each independently an integer from 1 to 6. The present embodiment is characterized in that the $R^1$ and $R^{1'}$ groups are attached to different chemical moieties.

In another embodiment of the present invention, a coordination polymer formed from the compound having Formula I is provided. In this embodiment, the coordination polymer includes a plurality of metal clusters and a plurality of organic linking ligands. Each linking ligand comprises a residue of a polydentate compound having Formula I.

In still another embodiment of the present invention, a coordination polymer formed from the compound having Formula II is provided. In this embodiment, the coordination polymer includes a plurality of metal clusters and a plurality of organic linking ligands. Each linking ligand comprises a residue of a polydentate compound having Formula II.

DETAILED DESCRIPTION OF THE PREFERRED EMBODIMENT(S)

Figure 1:
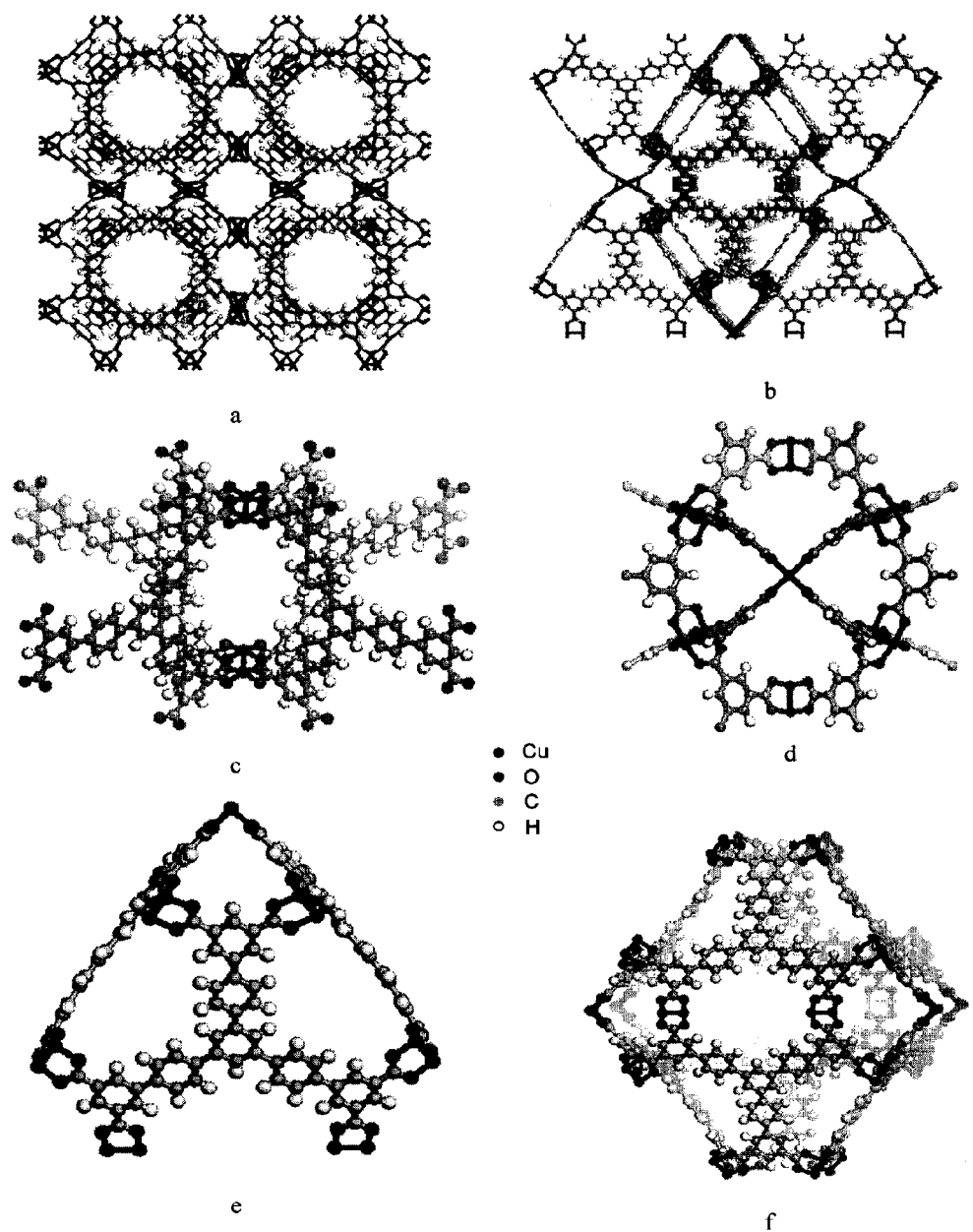
FIG. 1 is a ball and stick drawing illustrating the structure of the network of UMCM-450b.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. The description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application in their entirety to more fully describe the state of the art to which this invention pertains.

As used herein "linking ligand" means a chemical species (including neutral molecules and ions) that coordinate two or more metal atoms or metal clusters resulting in a predetermined separation, and the definition of void regions or channels in the framework that is produced. Examples include 4,4'-bipyridine (a neutral, multiple N-donor molecule) and benzene-1,4-dicarboxylate (a polycarboxylate anion).

As used herein "non-linking ligand" means a chemical species that is coordinated to a metal but does not link one metal cluster to another metal cluster.

As used herein "guest molecule" means any chemical species that resides within the void regions of an open framework solid. Examples include: molecules of the solvent that fill the void regions during the synthetic process, other molecules that are exchanged for the solvent such as during immersion (via diffusion) or after evacuation of the solvent molecules, such as gases in a sorption experiment.

As used herein "metal cluster" means any metal containing moiety present in a coordination polymer. This definition embracing single metal atoms or metal ions to groups of metals or metal ions that optionally include ligands or covalently bonded groups.

As used herein "heteroatom-containing aromatic ring system" means a substituted or unsubstituted functional group that includes aromatic ring systems containing 1 to 3 heteroatoms such as nitrogen, sulfur, and oxygen. Examples of aromatic ring systems containing 1 to 3 heteroatoms include, but are not limited to, furanyl, thienyl, and pridinyl group.

As used herein "alkynyl" as used herein means a substituted or unsubstituted hydrocarbon group that has at least one carbon to carbon triple bond.

As used herein "metal cation" means metal ions, metalloid ions, and metal-containing clusters As used herein "organic cation" means positively charged hydrocarbon containing ions such as ammonium cations, carbocations, oxonium cations, and phosphonium cations.

As used herein "aryl" means an aromatic ring such as phenyl, biphenyl, naphthyl, anthranyl, and the like.

As used herein "heteroaryl" means an aromatic ring system containing 1 to 3 heteroatoms such as nitrogen, sulfur, and oxygen. Examples of heteroaryl groups include, but are not limited to, furanyl, thienyl, and pridinyl group.

As used herein "alkyl aryl" means a substituted or unsubstituted functional group that includes an aromatic ring (e.g., phenyl, biphenyl, naphthyl, etc) with an attached $C_{1-8}$ alkyl group.

As used herein "alkyl heteroaryl" means a substituted or unsubstituted heteroaryl group with an attached $C_{1-8}$ g alkyl group.

As used herein "alkenyl" means a substituted or unsubstituted hydrocarbon group that has at least one carbon to carbon double bond.

As used herein "heteroatom-containing ring system" means a substituted or unsubstituted functional group that includes aromatic or aliphatic ring systems containing 1 to 3 heteroatoms such as nitrogen, sulfur, and oxygen.

As used herein "alkyl" means an aliphatic group such as methyl, ethyl, propyl, butyl, and the like.

Through the this application, when a group is described as substituted examples of substituents include, but are not limited to, nitro, halo, hydroxyl, ester, carboxylate, and the like.

In an embodiment of the present invention, a compound that is useful as a linking ligand or as a precursor for a linking ligand is provided. The compound of this embodiment is described by Formula I:

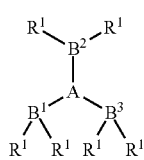

I wherein:
- $R^1$ is $CO_2R^2$, $CONR^2{}_2$, CN, alkynyl, or a $C_{4-18}$ heteroatom-containing aromatic ring system;
- $R^2$ is H, a metal cation, an organic cation, $C_{1-8}$ g alkyl, a $C_{6-18}$ aromatic ring system, or a $C_{4-18}$ heteroatom-containing aromatic ring system;
- A is a $C_{6-18}$ aromatic ring system or a $C_{4-18}$ heteroatom-containing aromatic ring system;
- $B^1$, $B^2$, $B^3$ are each independently a $C_{6-18}$ aromatic ring system, a $C_{4-18}$ heteroatom-containing ring system, $C_{7-18}$ alkyl aryl, or $C_{5-18}$ alkyl heteroaryl. In another variation, $B^1$, $B^2$, $B^3$ are the same. The aromatic ring systems, heteroatom-containing ring systems, $C_{1-8}$ alkyl, $C_{2-8}$ alkenyl, $C_{7-18}$ alkyl aryl, and $C_{5-18}$ alkyl heteroaryl groups are understood to be substituted or unsubstituted.

The compounds of Formula I are also defined by the positioning of $B^1$, $B^2$, $B^3$ about A. In a variation of this embodiment, the $B^1$, $B^2$, $B^3$ moieties are symmetrically distributed about the A moiety. In another variation, the center of masses of $B^1$, $B^2$, $B^3$ are each at least 4 angstroms from the center of mass of moiety A. In still another variation, the center of masses of $B^1$, $B^2$, $B^3$ are each at least 7 angstroms from the center of mass of moiety A. In yet another variation of the present embodiment, the center of masses of $B^1$, $B^2$, $B^3$ are each from about 7 to about 25 angstroms from the center of mass of moiety A.

In a particularly useful variation of the present embodiment, A is described by Formula IIIa;

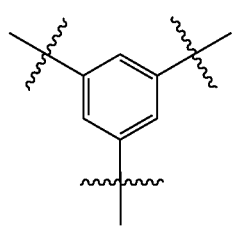

IIIa

In this formula, the squiggly line represents the position at which a bond to $B^1$, $B^2$, or $B^3$ is formed. In a further refinement of this variation, the compound is described by Formula IV:

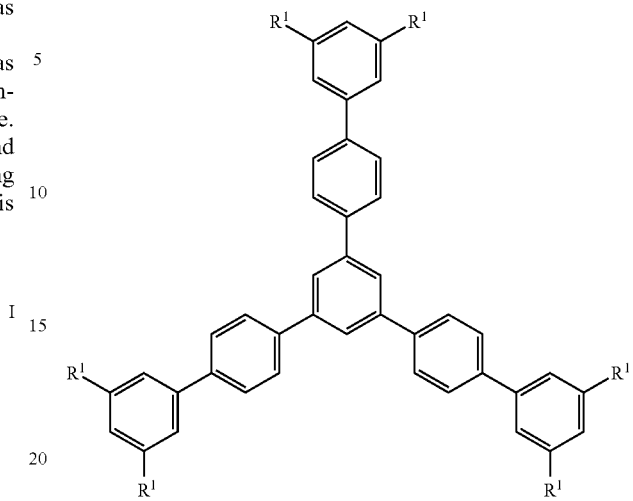

IV

In each of the compounds described by Formulae I, II, and IV a particularly useful compound results when $R^1$ is $CO_2R^2$, and in particular, when $R^1$ is $CO_2H$. A particularly useful compound includes 1,3,5-tris(3',5'-dicarboxybiphenyl-4-yl)benzene as a linking ligand.

In another embodiment of the present invention, another compound that is useful as a linking ligand or a precursor to a linking ligand for forming porous materials is provided. The compound of this embodiment is described by Formula II:

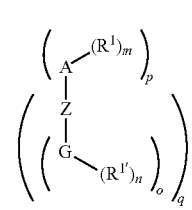

II wherein:
- $R^1$ and $R^{1'}$ are each independently $CO_2R^2$, $CONR^2{}_2$, CN, a $C_{2-8}$ alkynyl, or a $C_{4-18}$ heteroatom-containing aromatic ring system;
- $R^2$ is H, a metal cation, an organic cation, $C_{1-8}$ alkyl, a $C_{6-18}$ aromatic ring system, or a $C_{4-18}$ heteroatom-containing aromatic ring system;
- A and G are each independently a $C_{6-18}$ aromatic ring system or a $C_{4-18}$ heteroatom-containing aromatic ring system;
- Z is absent or a $C_{6-18}$ aromatic ring system or a $C_{4-18}$ heteroatom-containing aromatic ring system, $C_{7-18}$ alkyl aryl, $C_{5-18}$ heteroaryl, $C_{1-8}$ alkyl, $C_{2-8}$ alkenyl, or $C_{2-8}$ alkynyl; and
- m, n, o, p and q are each independently an integer from 1 to 6. In a variation, m, n, o, p and q are each independently an integer from 1 to 4. In another variation, m, n, o, p and q are each independently an integer from 1 to 3. The present embodiment is characterized in that the $R^1$ and $R^{1'}$ groups are attached to different chemical moieties. In this context, the term "different chemical moieties" means that the atoms (e.g., carbon atoms) that the groups are attached are not symmetric or are positioned in different chemical environments. For example if G and A are phenyl and if $R^1$ is in the para position, $R^{1'}$ will be in the meta or ortho positions. In a refinement, G is different from A.

A variation of the compound having Formula II is described by Formula V:

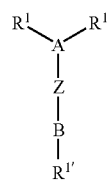

V wherein:

$R^1$ and $R^{1'}$ are each independently $CO_2R^2$, $CONR^2_2$, CN, alkynyl, or a $C_{4-18}$ heteroatom-containing aromatic ring system;

$R^2$ is H, a metal cation, an organic cation, $C_{2-8}$ alkyl, a $C_{6-18}$ aromatic ring system, or a $C_{4-18}$ heteroatom-containing aromatic ring system;

A and B are each independently a $C_{6-18}$ aromatic ring system or a $C_{4-18}$ heteroatom-containing aromatic ring system;

Z is absent or a $C_{6-18}$ aromatic rings system, a $C_{4-18}$ heteroatom-containing aromatic ring system, $C_{7-18}$ alkyl aryl, $C_{5-18}$ alkyl heteroaryl, $C_{1-8}$ alkyl, $C_{2-8}$ alkenyl, or $C_{2-8}$ alkynyl.

The compounds of Formula II and V are also defined by the relative positioning of A, B, G and Z. In a variation of formula II, A, G, and Z are arranged substantially linearly. In another variation, the center of mass of G is each at least 4 angstroms from the center of mass of moiety Z. In still another variation, the center of mass of G is at least 7 angstroms from the center of mass of moiety A. In yet another variation of the present embodiment, the center of mass of G is from about 4 to about 25 angstroms from the center of mass of moiety A. In a variation of formula V, A, B, and Z are arranged substantially linearly. In another variation, the center of mass of B is each at least 4 angstroms from the center of mass of moiety Z. In still another variation, the center of mass of B is at least 7 angstroms from the center of mass of moiety A. In yet another variation of the present embodiment, the center of mass of B is from about 4 to about 25 angstroms from the center of mass of moiety A.

In a particularly useful variation of the present embodiment, A is described by Formula IIIb:

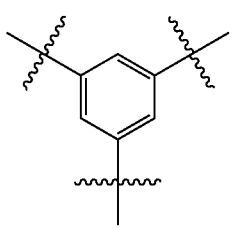

IIIb and B is described by Formula VI:

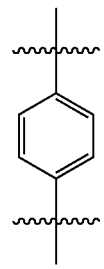

VI

In a particularly useful variation, the compounds of the present embodiment are described by Formulae VII, VIII, and IX:

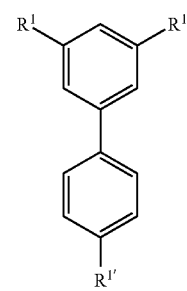

VII

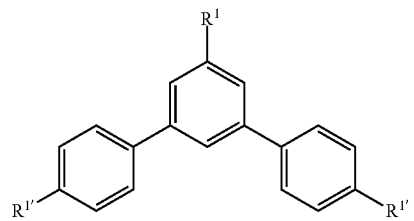

VIII

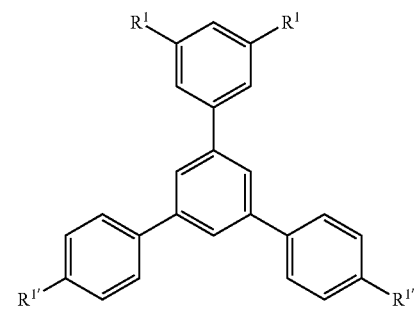

IX

In each of the compounds described by Formula I, II, IV, V, VII, VIII, and IX a particularly useful compound results when $R^1$ and $R^{1'}$ are $CO_2R^2$, and in particular, when $R^1$ and $R^{1'}$ is $CO_2H$.

In still another embodiment of the present invention, coordination polymers formed from the linking ligand compounds of Formula I, II, IV, V, VII, VIII and IX. These coordination polymers are useful for gas storage applications (e.g., hydrogen, carbon dioxide, carbon monoxide, and other adsorbable species as set forth herein). These coordination polymers define a molecular framework. In one variation of this embodiment, the coordination polymer comprises a plurality of metal clusters and a plurality of organic linking ligands, each linking ligand comprising a residue of a polydentate compound having Formula I:

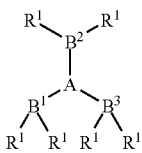

I

The details for $R^1$, A, $B^1$, $B^2$, and $B^3$ are the same as those set forth above.

In another variation of this embodiment, the coordination polymer comprises a plurality of metal clusters and a plurality of organic linking ligands, each linking ligand comprising a residue of a polydentate compound having Formula II:

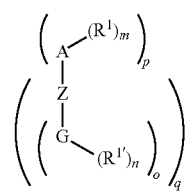

II

The details for $R^1$, $R^{1'}$, A, Z, G, m, n, o, p, and q are the same as those set forth above.

In a variation of the invention, the coordination polymers are characterized by having an average pore dimension from about 2 to 28 angstroms. In another variation, the coordination polymers are characterized by having an average pore dimension from about 5 to 20 angstroms. In still another variation, the coordination polymers are characterized by having an average pore dimension from about 8 to 18 angstroms. In yet another variation of the present invention, the coordination polymers are characterized by having surface area greater than about 2000 $m^2/g$ as determined by the Langmuir method. In yet another variation of the present invention, the coordination polymers are characterized by having surface area from about 1000 to about 6000 $m^2/g$ as determined by the Langmuir method.

In a refinement of the present embodiment, the coordination polymer further includes at least one non-linking ligand. Examples of useful non-linking ligands include, but are not limited to, oxide, peroxide, superoxide, hydroxide, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite, and combinations thereof.

In another refinement of the present embodiment, the coordination polymer further includes an adsorbed chemical species. Examples of useful adsorbed chemical species include, but are not limited to, ammonia, carbon dioxide, carbon monoxide, hydrogen, amines, methane, oxygen, argon, nitrogen, argon, organic dyes, polycyclic organic molecules, and combinations thereof.

In yet another refinement of the present invention, the metal cluster includes at least one metal ion. Suitable metal ions are selected from the group consisting Group 1 through 16 metals of the IUPAC Periodic Table of the Elements including actinides, lanthanides, and combinations thereof.

In yet another refinement, the metal cluster further includes at least one atom from the group consisting of N, P, As, Sb, Bi, O, S, Se, Te, F, Cl, Br, I. These atoms are anionic and balance the electric charge of the metal cluster.

In still another refinement of the present embodiment, the coordination polymer further includes one or more guest molecules occupying the space within the framework. Examples of guest molecules include, but are not limited to, solvents, gases, amines, organic compounds, coordination compounds, polymers, organic particles, organometallic particles, inorganic particles, and combinations thereof. More specific examples of guest molecules include, but are not limited to, small organic alkanes, arenes, ethers, haloalkanes, esters, amides, sulfides, sulfoxides, amines, ketones, aldehydes, alcohols, thiols, hydrogen, ammonia, methane, oxygen, nitrogen, argon, carbon monoxide, carbon dioxide, nitrous oxide, sulfur dioxide, sulfur trioxide, ethylene, acetylene, and combinations thereof.

The coordination polymers include a number of useful combinations of ligands derived from structure I, II, III, V, VII, VIII, and IX. For example, one useful polymer has a formula of $[(C_{48}H_{24}O_{12})Cu_3.(solvent)_n]_x$ where x is a real number and n is a number from 0 to about 50. Another useful compound comprises biphenyl-3,4',5-tricarboxylate molecules linked together by metal cluster having one of more metal ions. This structure is referred to herein as "UMCM-150." The material referred to as UMCM-150 includes the cluster $[Cu_2(O_2CR)_4]$ and the trinuclear cluster, $[Cu_3(O_2CR)_6]$ (R in this context is the linker minus the two carboxyl groups as set forth above). Still another useful coordination polymer comprises multiple 1,3,5-tris(3',5'-dicarboxybiphenyl-4-yl)benzene molecules linked together by multiple of metal clusters having one of more metal ions. This structure is referred to herein as "UMCM-450b." Another example is a coordination polymer having the following formula $[(C_{15}H_7O_6)_2Cu_3.(solvent)_n]_x$ where x is a real number and n is a number from 0 to 50.

In still another embodiment of the present invention, a method of forming the linking ligand compounds and coordination polymers set forth above is provided. The preparation of a compound having formula XII is provided in Scheme 1.

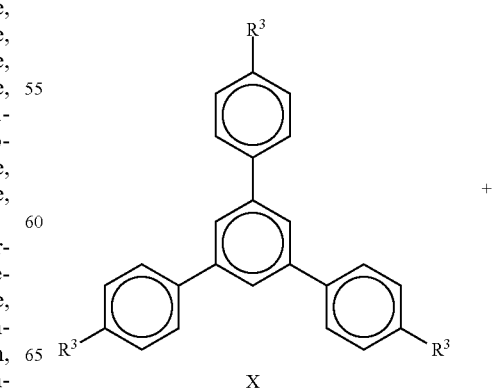

Scheme 1

-continued

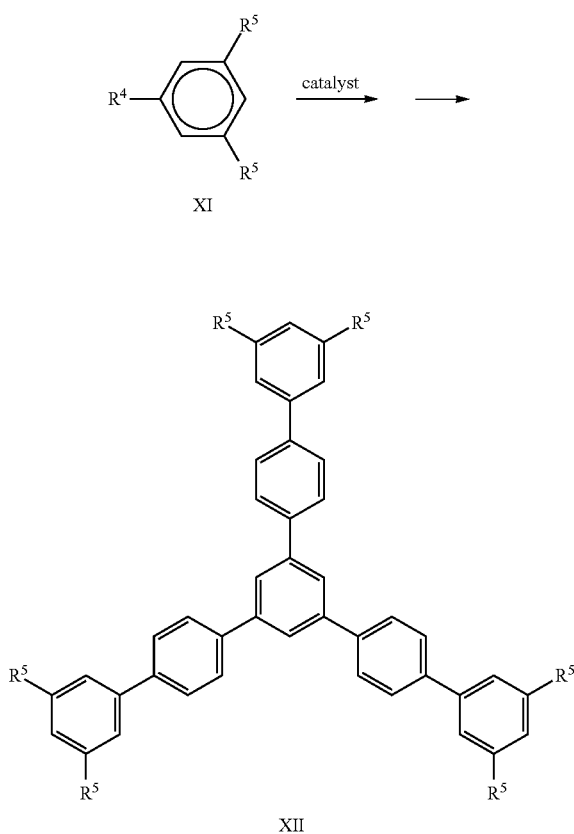

XI

XII

Scheme 2

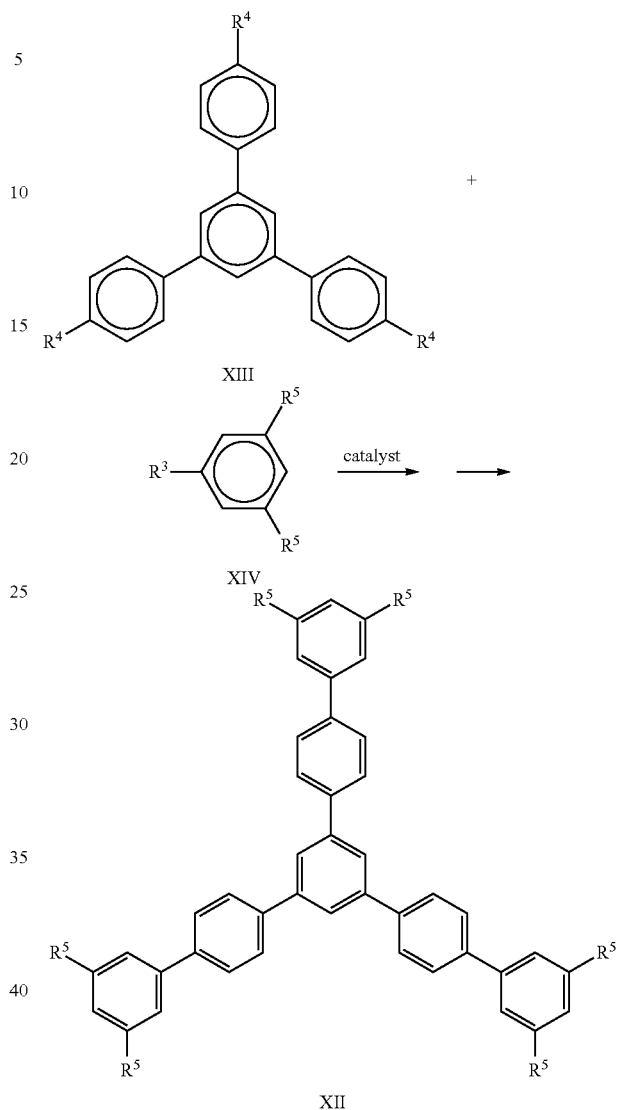

XIII

XIV

XII

In accordance with Scheme 1, a compound having formula X and a coupling partner having formula XI are combined in the presence of a transition metal catalyst to form a compound having formula XII. After reaction has occurred, an appropriate workup is performed. This workup includes, for example, acid- or base-mediated hydrolysis, oxidation, reduction, or ozonolysis. The substituents for Scheme 1 are as follows:

$R^3$ is F, Cl, Br, I, $OSO_2R^8$, or $N_2^+X^{1-}$;

$R^4$ is $B(OR^7)_2$, $BF_3^-M^+$, $SnR^8{}_3$, $Si(OR^8)_3SiR^8{}_2F$, $ZnX^2$, $MgX^2$, $C_{1-8}$ alkyl, $C_{1-8}$ perfluoroalkyl, $C_{2-8}$ alkene, $C_{2-8}$ alkyne, or a $C_{4-18}$ heteroatom-containing ring system;

$R^5$ is $CO_2R^{10}$, $CONR^{11}{}_2$, CN, alkynyl, or a heteroatom-containing ring system;

$R^7$ is H, $C_{1-8}$ alkyl, $C_{5-18}$ cyclic alkyl, a $C_{6-18}$ aromatic ring system, or a $C_{4-18}$ heteroatom-containing ring system;

$R^8$ is $C_{1-8}$ alkyl, $C_{1-8}$ perfluoroalkyl, a $C_{6-18}$ aromatic ring system, or a $C_{4-18}$ heteroatom-containing ring system;

$R^{10}$ is H, a metal cation, an organic cation, $C_{1-8}$ alkyl, a $C_{6-18}$ aromatic ring system, a $C_{4-18}$ heteroatom-containing ring system, $R^{11}$ is H, $C_{1-8}$ alkyl, cyclic $C_{5-18}$ alkyl, a $C_{6-18}$ aromatic ring system, or a $C_{4-18}$ heteroatom-containing ring system, $X^1$ is an organic or inorganic anion;

$X^2$ is Cl, Br, I, OTF; and

M is an organic or inorganic cation.

With reference to Scheme 2, another synthetic route to a compound having formula XII is provided:

In accordance with Scheme 2, a compound having formula XIII and a coupling partner having formula XIV are combined in the presence of a transition metal catalyst to form a compound having formula XII. After reaction has occurred, an appropriate workup is performed. This workup includes, for example, acid- or base-mediated hydrolysis, oxidation, reduction, or ozonolysis. The substituents for Scheme 2 are as follows:

$R^3$ is F, Cl, Br, I, $OSO_2R^8$, $N_2^+X^{1-}$;

$R^4$ is $B(OR^7)_2$, $BF_3^-M^+$, $SnR^8{}_3$, $Si(OR^8)_3SiR^8{}_2F$, $ZnX^2$, $MgX^2$, $C_{1-8}$ alkyl, $C_{1-8}$ perfluoroalkyl, $C_{2-8}$ alkenyl, $C_{2-8}$ alkynyl, or a $C_{4-18}$ heteroatom-containing ring system;

$R^5$ is $CO_2R^{10}$, $CONR^{11}{}_2$, CN, alkynyl, or a heteroatom-containing ring system;

$R^7$ is H, $C_{1-8}$ alkyl, cyclic $C_{5-18}$ alkyl, a $C_{6-18}$ aromatic ring system, or a $C_{4-18}$ heteroatom-containing ring system;

$R^8$ is $C_{1-8}$ alkyl, $C_{1-8}$ perfluoroalkyl, a $C_{6-18}$ aromatic ring system, or a $C_{4-18}$ heteroatom-containing ring system;

$R^{10}$ is H, a metal cation, an organic cation, alkyl, a $C_{6-18}$ aromatic ring system, or a $C_{4-18}$ heteroatom-containing ring system, $R^{11}$ is H, $C_{1-8}$ alkyl, cyclic $C_{5-18}$ alkyl, a $C_{6-18}$ aromatic ring system, or a $C_{4-18}$ heteroatom-containing ring system, $X^1$ is an organic or inorganic anion;

$X^2$ is Cl, Br, I, or OTF;

M is an organic or inorganic cation;

With reference to Scheme 3, another synthetic route to a compound having formula XII is provided:

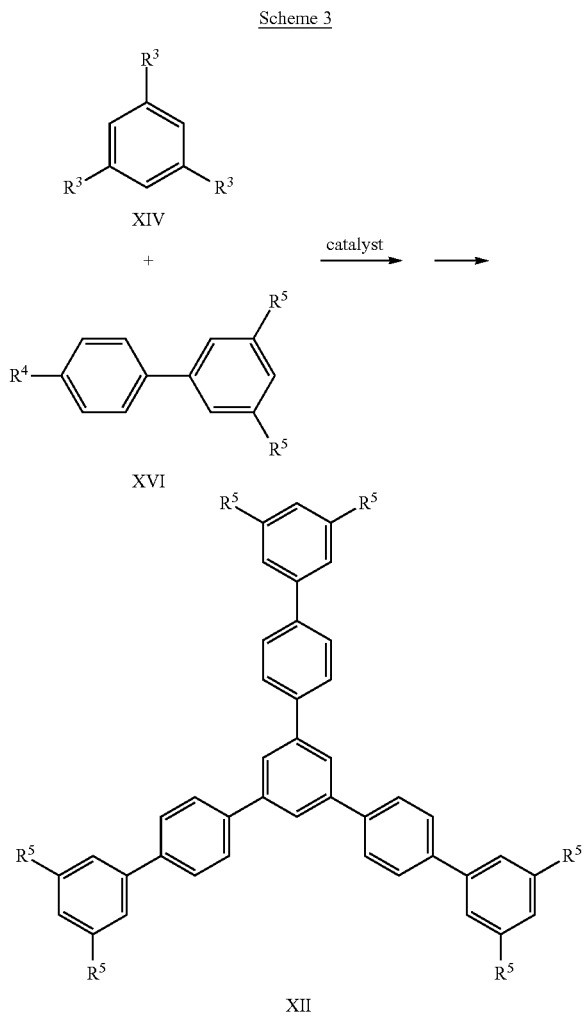

Scheme 3

In accordance with Scheme 3, a compound having formula XV and a coupling partner having formula XVI are combined in the presence of a transition metal catalyst. After reaction has occurred, an appropriate workup is performed. This workup includes, for example, acid- or base-mediated hydrolysis, oxidation, reduction, or ozonolysis. The substituents for Scheme 3 are as follows:

$R^3$ is F, Cl, Br, I, $OSO_2R^8$, or $N_2^+X^{1-}$;

$R^4$ is $B(OR^7)_2$, $BF_3^-M^+$, $SnR^8{}_3$, $Si(OR^8)_3SiR^8{}_2F$, $ZnX^2$, $MgX^2$, $C_{1-8}$ alkyl, $C_{1-8}$ perfluoroalkyl, $C_{2-8}$ alkene, $C_{2-8}$ alkyne, or a $C_{4-18}$ heteroatom-containing ring system;

$R^5$ is $CO_2R^{10}$, $CONR^{11}{}_2$, CN, $C_{2-8}$ alkynyl, or $C_{6-18}$ heteroatom-containing ring system;

$R^7$ is H, $C_{1-8}$ alkyl, cyclic $C_{5-18}$ alkyl, a $C_{6-18}$ aromatic ring system, or a $C_{4-18}$ heteroatom-containing ring system;

$R^8$ is $C_{1-8}$ alkyl, $C_{1-8}$ perfluoroalkyl, a $C_{6-18}$ aromatic ring system, a $C_{4-18}$ heteroatom-containing ring system;

$R^{10}$ is H, a metal cation, organic cation, $C_{1-8}$ alkyl, perfluoroalkyl, a $C_{6-18}$ aromatic ring system, or a $C_{4-18}$ heteroatom-containing ring system, $R^{11}$ is H, $C_{1-8}$ alkyl, cyclic $C_{5-18}$ alkyl, $C_{1-8}$ perfluoroalkyl, a $C_{6-18}$ aromatic ring system, or a $C_{4-18}$ heteroatom-containing ring system;

$X^1$ is an organic or inorganic anion;

$X^2$ is Cl, Br, I, OTF; and

M is an organic or inorganic cation.

With reference to Scheme 4, another synthetic route to a compound having formula XII is provided:

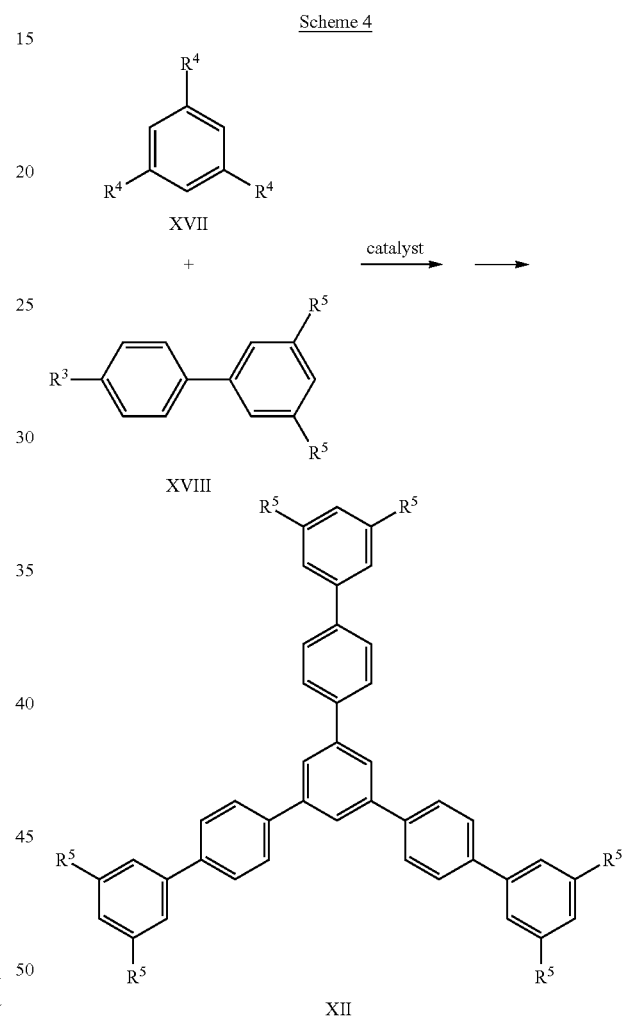

Scheme 4

In accordance with Scheme 4, a compound having formula XVII and a coupling partner having formula XVIII are combined in the presence of a transition metal catalyst to form a compound having formula XII. After reaction has occurred, an appropriate workup is performed. This workup includes, for example, acid- or base-mediated hydrolysis, oxidation, reduction, or ozonolysis. The substituents for Scheme 4 are as follows:

$R^3$ is F, Cl, Br, I, $OSO_2R^8$, or $N_2^+X^{1-}$;

$R^4$ is $B(OR^7)_2$, $BF_3^-M^+$, $SnR^8{}_3$, $Si(OR^8)_3SiR^8{}_2F$, $ZnX^2$, $MgX^2$, $C_{1-8}$ alkyl, $C_{1-8}$ perfluoroalkyl, $C_{2-8}$ alkene, $C_{2-8}$ alkyne, or a $C_{4-18}$ heteroatom-containing ring system;

$R^5$ is $CO_2R^{10}$, $CONR^{11}{}_2$, CN, $C_{2-8}$ alkynyl, or $C_{4-18}$ heteroatom-containing ring system;

$R^7$ is H, $C_{1-8}$ alkyl, cyclic $C_{1-8}$ alkyl, a $C_{6-18}$ aromatic ring system, or $C_{4-18}$ heteroatom-containing ring system;

$R^8$ is $C_{1-8}$ alkyl, $C_{1-8}$ perfluoroalkyl, a $C_{6-18}$ aromatic ring system, or a $C_{4-18}$ heteroatom-containing ring system;

$R^{10}$ is H, a metal cation, an organic cation, alkyl, a $C_{6-18}$ aromatic ring system, a $C_{4-18}$ heteroatom-containing ring system, $R^{11}$ is H, $C_{2-8}$ alkyl, cyclic alkyl, a $C_{6-18}$ aromatic ring system, or a $C_{4-18}$ heteroatom-containing ring system, $X^1$ is an organic or inorganic anion;

$X^2$ is Cl, Br, I, OTF; and

M is an organic or inorganic cation.

With reference to Scheme 5, another synthetic route to compound XII is provided:

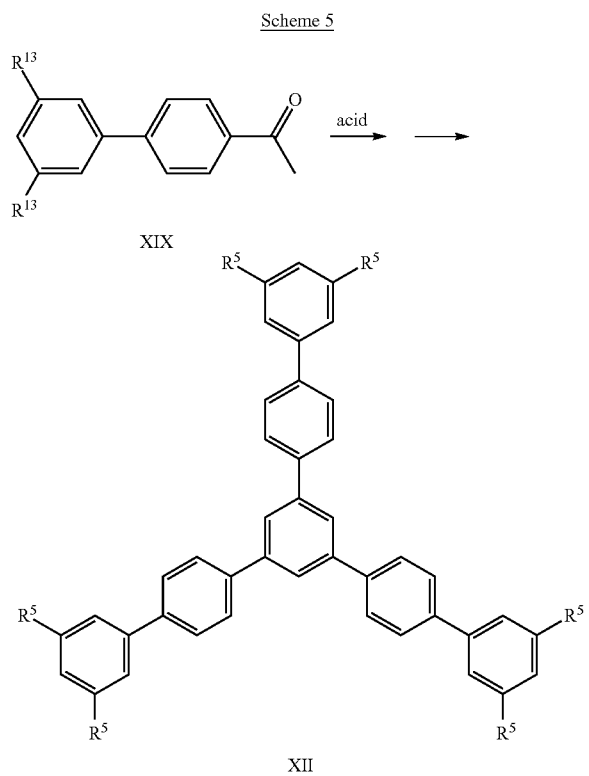

In accordance with Scheme 5 compound XIX is cyclotrimerized with a Lewis acid or a Bronsted base to form compound XII. Examples of suitable Lewis acids include $X^2_4$ $SnX^2_4TiX^2_4ZrX^2_4BX^2_3AlX^2_3GaX^2_3$ where $X^2$ is Cl, Br, I, Otf. Examples of suitable Bronsted acids are TfOH, ClSO$_3$H, and FSO$_3$H. After reaction has occurred, an appropriate workup is performed. This workup includes, for example, acid- or base-mediated hydrolysis, oxidation, reduction, or ozonolysis. The substituents for Scheme 3 are as follows:

$R^{13}$ is $CO_2R^{14}$, $CONR^{15}_2$, CN, a $C_{2-8}$ alkynyl, or a $C_{4-18}$ heteroatom-containing ring system;

$R^{14}$ is H, a metal cation, an organic cation, a $C_{1-8}$ alkyl, a $C_{1-8}$ perfluoroalkyl, a $C_{6-18}$ aromatic ring system, or a $C_{4-18}$ heteroatom-containing ring system;

$R^{15}$ is H, a $C_{1-8}$ alkyl, cyclic a $C_{6-18}$ alkyl, perfluoroalkyl, a $C_{4-18}$ aromatic ring system, or a $C_{4-18}$ heteroatom-containing ring system; and $R^{16}$ is a $C_{1-8}$ alkyl, a $C_{1-8}$ perfluoroalkyl, a $C_{6-18}$ aromatic ring system, or a $C_{4-18}$ heteroatom-containing ring system.

With reference to Scheme 6, a synthetic route to a compound XXII is provided:

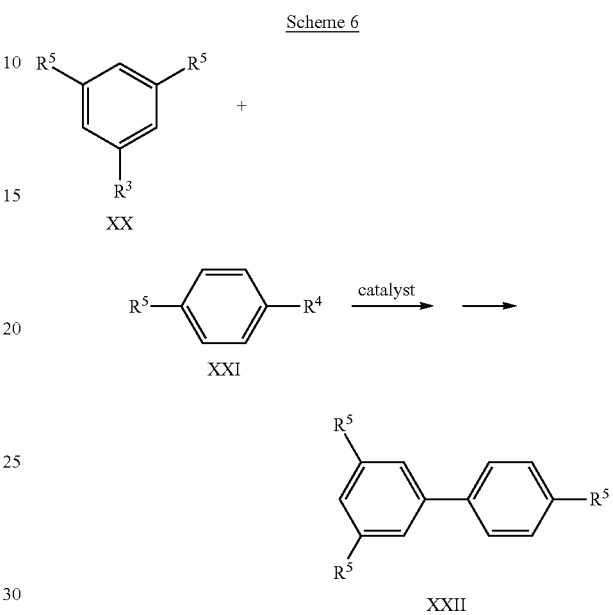

In accordance with Scheme 6, a compound having formula XX and a coupling partner having formula XXI are combined in the presence of a transition metal catalyst to form a compound having formula XXII. After reaction has occurred, an appropriate workup is performed. This workup includes, for example, acid- or base-mediated hydrolysis, oxidation, reduction, or ozonolysis. The substituents for Scheme 6 are as follows:

$R^3$ is F, Cl, Br, I, $OSO_2R^8$, or $N_2^+X^{1-}$;

$R^4$ is $B(OR^7)_2$, $BF_3^-M^+$, $SnR^8_3$, $Si(OR^8)_3SiR^8_2F$, $ZnX^2$, $MgX^2$, $C_{1-8}$ alkyl, $C_{1-8}$ perfluoroalkyl, $C_{2-8}$ alkene, $C_{2-8}$ alkyne, or a $C_{4-18}$ heteroatom-containing ring system;

$R^5$ is $CO_2R^{10}$, $CONR^{11}_2$, CN, $C_{2-8}$ alkynyl, or a $C_{4-18}$ heteroatom-containing ring system;

$R^7$ is H, a $C_{1-8}$ alkyl, cyclic a $C_{5-18}$ alkyl, a $C_{6-18}$ aromatic ring system, or a $C_{4-18}$ heteroatom-containing ring system;

$R^8$ is a $C_{1-8}$ alkyl, a $C_{1-8}$ perfluoroalkyl, a $C_{6-18}$ aromatic ring system, or a $C_{4-18}$ heteroatom-containing ring system;

$R^{10}$ is H, a metal cation, an organic cation, a $C_{1-8}$ alkyl, a $C_{6-18}$ aromatic ring system, a $C_{4-18}$ heteroatom-containing ring system, $R^{11}$ is H, a $C_{1-8}$ alkyl, a $C_{5-18}$ cyclic alkyl, a $C_{6-18}$ aromatic ring system, or a $C_{4-18}$ heteroatom-containing ring system, $X^1$ is an organic or inorganic anion;

$X^2$ is Cl, Br, I, OTF; and

M is an organic or inorganic cation.

With reference to Scheme 7 another synthetic route to a compound XXII is provided:

17

Scheme 7

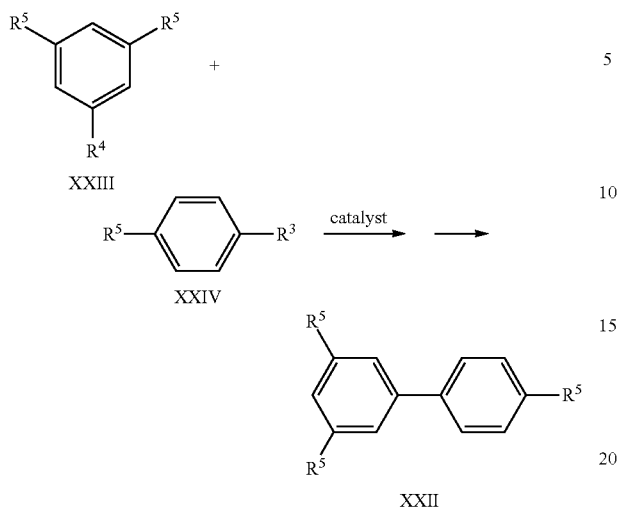

In accordance with Scheme 7, a compound having formula XXIII and a coupling partner having formula XXIV are combined in the presence of a transition metal catalyst to form a compound having formula XXII. After reaction has occurred, an appropriate workup is performed. This workup includes, for example, acid- or base-mediated hydrolysis, oxidation, reduction, or ozonolysis. The substituents for Scheme 4 are as follows:

$R^3$ is F, Cl, Br, I, $OSO_2R^8$, or $N_2^+X^{1-}$;

$R^4$ is $B(OR^7)_2$, $BF_3^-M^+$, $SnR^8_3$, $Si(OR^8)_3 SiR^8_2F$, $ZnX^2$, $MgX^2$, $C_{1-8}$ alkyl, $C_{1-8}$ perfluoroalkyl, $C_{2-8}$ alkene, $C_{2-8}$ alkyne, or $C_{4-18}$ heteroatom-containing ring system;

18

$R^5$ is $CO_2R^{10}$, $CONR^{11}_2$, CN, $C_{2-8}$ alkynyl, or a $C_{4-18}$ heteroatom-containing ring system;

$R^7$ is H, a $C_{1-8}$ alkyl, a $C_{5-18}$ cyclic alkyl, a $C_{6-18}$ aromatic ring system, or a $C_{4-18}$ heteroatom-containing ring system;

$R^8$ is a $C_{1-8}$ alkyl, a $C_{1-8}$ perfluoroalkyl, a $C_{6-18}$ aromatic ring system, or a $C_{4-18}$ heteroatom-containing ring system;

$R^{10}$ is H, a metal cation, an organic cation, a $C_{1-8}$ alkyl, a $C_{6-18}$ aromatic ring system, a $C_{4-18}$ heteroatom-containing ring system, $R^{11}$ is H, a $C_{1-8}$ alkyl, a $C_{5-18}$ cyclic alkyl, a $C_{6-18}$ aromatic ring system, or a $C_{4-18}$ heteroatom-containing ring system, $X^1$ is an organic or inorganic anion;

$X^2$ is Cl, Br, I, OTF; and

M is an organic or inorganic cation.

With reference to Scheme 8, another synthetic route to biphenyl-3,4',5-tricarboxylic acid is provided:

Scheme 8

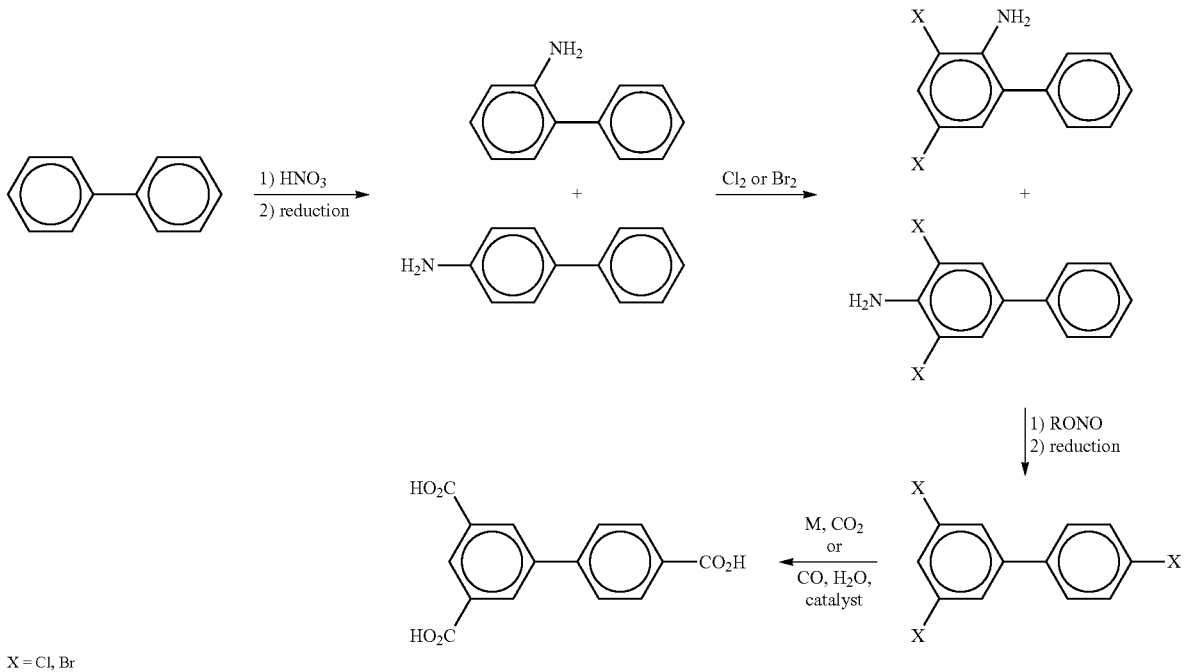

X = Cl, Br

In accordance with Scheme 8, nitration of biphenyl using nitric acid/sulfuric acid, fuming nitric acid, or nitric acid/acetic acid results in a mixture of 2- and 4-nitrobiphenyl. This mixture is then reduced to 2- and 4-aminobiphenyl using one of the following conditions: $H_2$/hydrazine/formic acid/cyclohexene and a transition metal catalyst (nickel, palladium, platinum, rhodium or ruthenium; Fe powder/AcOH; Zn powder/HCl; Sn/HCl; $SnCl_2$; $LiAlH_4$; $Na_2S$; $Na_2S_2O_4$; Sm; PHMS/Pd). The resulting compound is halogenated using $Cl_2$ or $Br_2$ in a suitable solvent to yield a mixture of 2-amino-3, 4',5-trichlorobiphenyl and 4-amino-3,4',5-trichlorobiphenyl or 2-amino-3,4',5-tribromobiphenyl and 4-amino-3,4',5-tribromobiphenyl. The resulting compound is then diazotized using a nitrite (R is H, Na, K, alkyl, or aryl), followed by reduction using one of the following: $H_2$/transition metal catalyst (metal=nickel, palladium, platinum, rhodium or ruthenium); $H_3PO_2$; hydroquinone; formaldehyde; $Cu_2O$/EtOH; Zn/EtOH; $NaBHR^{17}_3$ (where $R^{17}$ is H, alkoxy, alkyl, or acyl); $LiAlHR^{17}_3$ (where $R^{17}$ is H, alkoxy, alkyl, or acyl); tetramethylurea; ROM/ROH (where $R^{18}$ is H or alkyl and M is alkali or alkaline earth metal); $R^{18}_3N/R^{19}OH$ (where $R^{18}$ and $R^{19}$ are H or alkyl); PhSH; $R^{20}_3SnH$ (where $R^{20}$ is alkyl or aryl); $R^{20}MgX$ (where $R^{20}$ is alkyl or aryl and X is Cl, Br, I); Sn/HCl; $Na_2SnO_2$; $R^{18}_3SiX/THF/R^{19}_2NCHO$ (where $R^{18}$ and $R^{19}$ is H or alkyl, and X is Cl, Br, or I); $FeSO_4$/$R^{18}CONR^{19}_2$ (where $R^{18}$ and $R^{19}$ are H or alkyl); PHMS; $HSiCl_3$; $H_2O_2/H_2O/THF$.

In the next step, metalation of 3,4',5-trichlorobiphenyl or 3,4',5-tribromobiphenyl is accomplished using Mg metal; Li metal; iPrMgX where X=Cl, Br, I; $R^{21}Li$ (where $R^{21}$ is alkyl) followed by quenching with: $CO_2$; $CO(OR^{22})_2$ (where $R^{22}$ is alkyl or aryl); $XCO_2R^{22}$ (where X is F, Cl, CN, $RO_2CO$ and $R^{22}$ is alkyl or aryl); $HCOX^1$ (where $X^1$ is =F, Cl, SR, OR, $HCO_2$, or $NR_2$). This step may be followed by acidification, acid- or base-mediated hydrolysis or oxidation. Finally, 3,4',5-trichlorobiphenyl or 3,4',5-tribromobiphenyl are catalytically carbonylated of using CO, $R^{23}OH$ (where $R^{23}$ is H, $C_{1-8}$ alkyl, $C_{1-8}$ perfluoroalkyl, $C_{6-18}$ aryl, or a $C_{4-18}$ heteroatom-containing ring system) and a transition metal catalyst. This step may be followed by acidification, or acid- or base-mediated hydrolysis.

In a variation of the invention, the coordination polymers set forth above are formed by reacting the linking ligand compounds set forth by Formulae I-VII with a suitable source of metal clusters. Typically, the source of metal clusters and the linking ligand compounds are combined in solution. The source of metal cluster usually forms a solution containing metal ions when in solution.

The following examples illustrate the various embodiments of the present invention. Those skilled in the art will recognize many variations that are within the spirit of the present invention and scope of the claims.

EXAMPLES

1. Synthesis of 1,3,5-tris(3',5'-dicarboxybiphenyl-4-yl)benzene and UMCM-450b

Organic ligand (1,3,5-tris(3',5'-dicarboxybiphenyl-4-yl) benzene) is synthesized by Suzuki coupling of 1,3,5-tris(4-bromophenyl)benzene with dimethyl isophthalate-5-pinacolboronate, followed by hydrolysis of the ester groups using KOH in dioxane/$H_2O$ and acidic workup. This route afforded compound (1,3,5-tris(3',5'-dicarboxybiphenyl-4-yl)benzene) in an unoptimized 54% yield.

1,3,5-tris(3',5'-dicarboxybiphenyl-4-yl)benzene 1,3,5-Tris(4-bromophenyl)benzene (0.980 g, 1.81 mmol), dimethyl isophthalate-5-pinacolboronate (2.08 g, 6.50 mmol), $K_3PO_4$ (tribasic, 3.84 g, 18.1 mmol) and 1,4-dioxane (100 mL) are added into a 200 mL round-bottomed flask equipped with a magnetic stirrer and water jacketed condenser. The resulting suspension is degassed for 15 min. by sparging with nitrogen gas. $Pd(PPh_3)_4$ (0.157 g, 0.136 mmol) is added, and the mixture is heated to reflux overnight under a nitrogen atmosphere. After cooling to room temperature, the reaction mixture is poured in $H_2O$ (100 mL) and the precipitate is collected by filtration and washed with a minimal amount of THF. The crude material is dissolved in dioxane/$H_2O$ (10:1, 110 mL), KOH (1.72 g, 30.6 mmol) is added and the mixture is heated to reflux for 12 hours. The solvent is removed by evaporation and the residue is dissolved in $H_2O$ (100 mL). The residual solids are filtered off and the filtrate is acidified with concentrated HCl (20 mL). The target compound is collected by filtration, washed with $H_2O$ and acetone and dried under vacuum to yield 0.783 g of 1 (0.980 mmol as a white powder, 54%): mp>300° C.; $^1$H NMR (400 MHz, DMSO-$d_6$): δ 13.39 (s, 6H), 8.43 (s, 3H), 8.42 (s, 6H), 8.04 (d, $^3J$=8.2 Hz, 6H), 8.02 (s, 3H), 7.86 (d, $^3J$=8.2 Hz, 6H) ppm; $^{13}$C NMR (100 MHz, DMSO-$d_6$): δ 166.9, 141.4, 140.9, 140.3, 138.1, 132.5, 131.6, 129.3, 128.4, 127.8, 124.9 ppm; HRMS (EI) calcd. for $C_{48}H_{30}O_{12}$ (m/e): 798.1737. found: 798.1751.

UMCM-450b 1,3,5-tris(3',5'-dicarboxybiphenyl-4-yl)benzene (0.0500 g, 0.0626 mmol), concentrated HCl (0.025 mL) and $Cu(NO_3)_2.2.5H_2O$ (0.0705 g, 0.376 mmol) are added in DMF/dioxane/$H_2O$ (10:4:1, 15 mL) and the solids are dissolved with heating. The solution is placed in a tightly screwed 20 mL vial and heated at 85° C. for 18 h. The mother liquor is removed and replaced twice with fresh DMF and then with acetone. The acetone is replaced with fresh solvent three times over a period of three days. The crystals are then placed in a Schlenk tube and dried under vacuum at ambient temperature until the material started to change color to deep purple. The crystals are further evacuated at 100° C. under vacuum for 1-2 h to yield 0.0390 g of activated UMCM-450b (0.0357 mmol as blue-green crystals, 57% based on the formula determined by elemental analysis): mp>300° C. (dec.); PXRD (Cu-κα1, 1.5418 Å) 2θ (°) approx. 3.1 (100%), 6.1 (22%), 7.3 (15%), 8.2 (11%), 9.6 (25%), 11.1 (11%), 12.1 (8%), 12.9 (18%); Anal. calcd. for $C_{48}H_{24}O_{12}Cu_3$.1.5 DMF: C, 57.69; H, 3.18; N, 1.92. found: C, 57.31; H, 2.93; N, 2.30.

Figure 2:
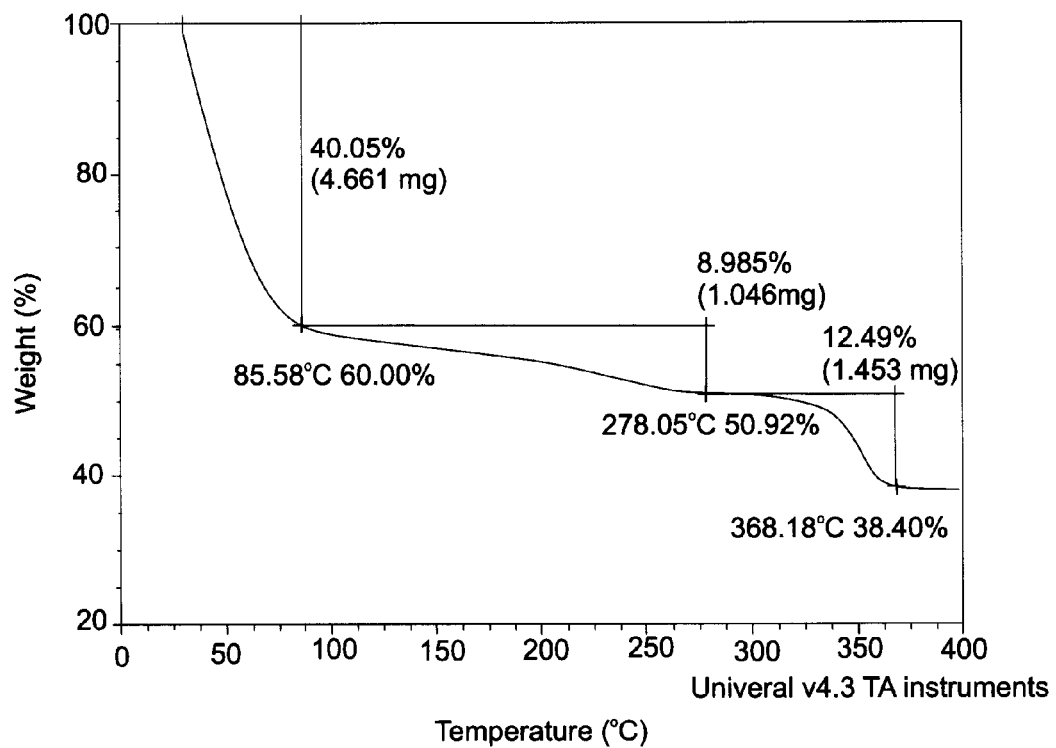
FIG. 2 provides the thermal gravimetric analysis (TGA) of UMCM-450b where the guest solvent has been exchanged with acetone prior to analysis. Percentages of weight loss and the corresponding temperatures are shown.

X-ray diffraction of a single crystal of UMCM-450b revealed a cubic structure (Space group Fm-3m, with a approximately equal to 47.3 Å) (FIGS. 1a-b) where each organic linker molecule is bound to nine neighboring linker molecules through six $Cu_2$(carboxylate)$_4$ clusters, a pair of Cu clusters binding three neighbor molecules (FIG. 1c). The crystal structure is comprised of three different types of cage-like compartments: spherical cages formed by 24 organic linker molecules linked together through 12 Cu clusters (FIG. 2d), tetrahedral cages where each face corresponds to a linker molecule and each vertex is bound to a spherical cage (FIG. 1e), and octahedral cages where each face corresponds to a linker molecule and each vertex is bound to a spherical cage (FIG. 1f).

Thermal gravimetric analysis (TGA) of a sample of UMCM-450b exchanged with acetone (11.6360 mg) heated at a rate of 5° C./min from 25 to 400° C. (FIG. 2) showed an initial weight loss corresponding to about 40% between about 25 and 85° C., which can be attributed to loss of guest solvent. A weight loss of about 9% between about 85 and 280° C. may correspond to the loss of solvent molecules bound more tightly to the Cu atoms. Finally, a weight loss of about 12.5% above 300° C. is observed.

Figure 3:
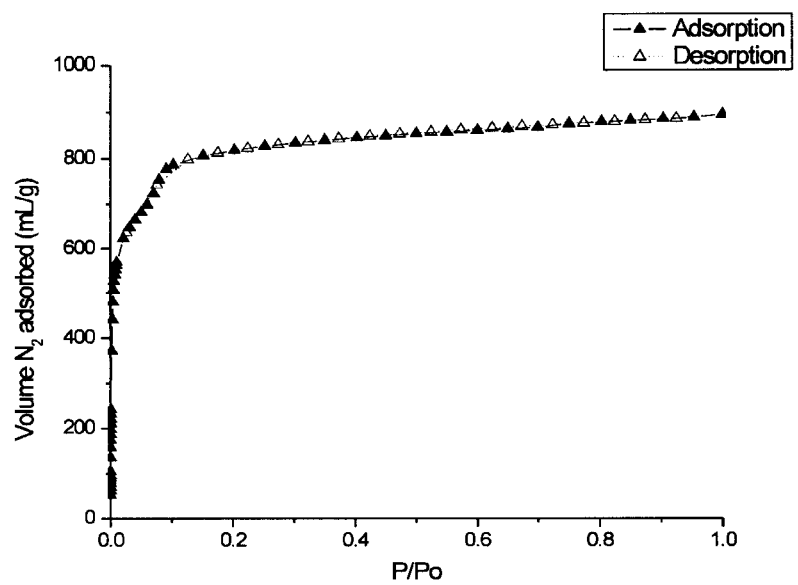
FIG. 3 is a plot of the nitrogen gas sorption isotherm at 77 K for UMCM-450b (filled triangles, adsorption; open triangles, desorption)
Figure 4:
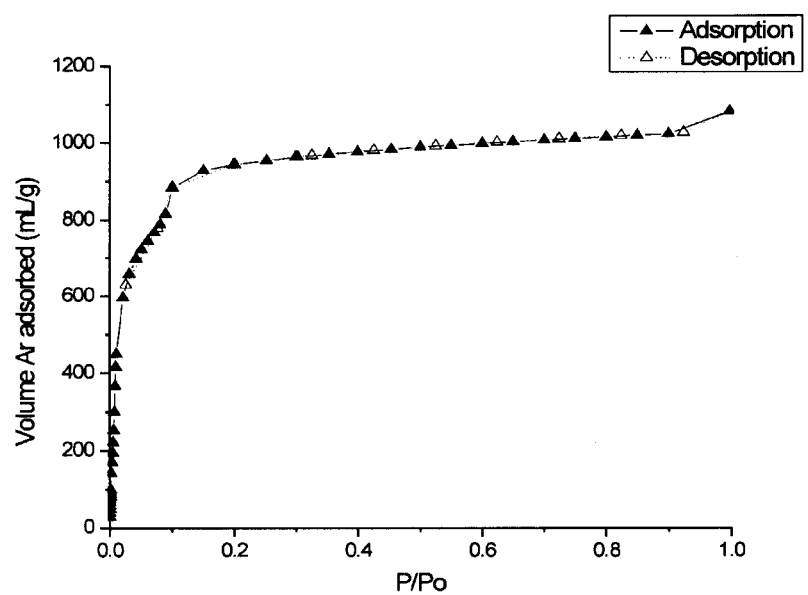
FIG. 4 is a plot of the argon gas sorption isotherm at 87 K for UMCM-450b (filled triangles, adsorption; open triangles, desorption)
Figure 5:
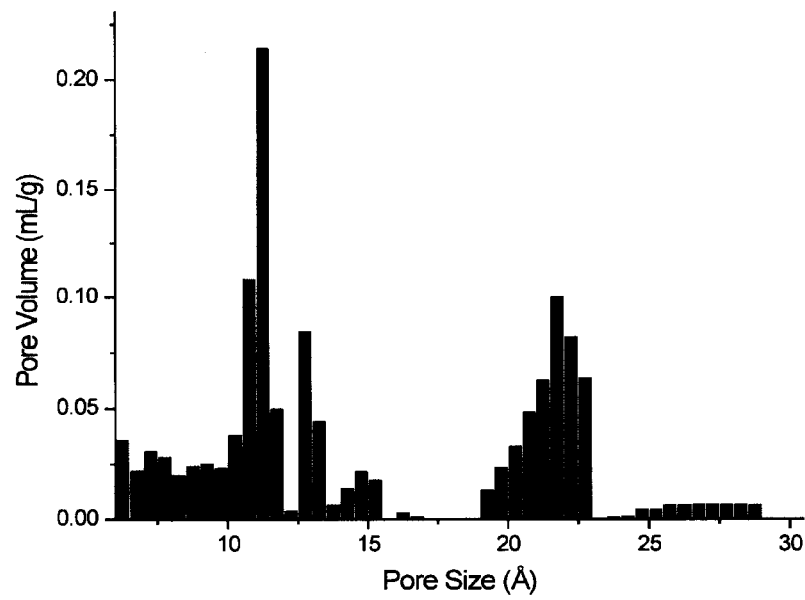
FIG. 5 is a histogram of the pore size distribution for UMCM-450b and Pore size distribution is determined from the argon isotherm at 87 K.

The $N_2$ sorption isotherm is measured on an evacuated sample of UMCM-450b. The isotherm showed a type IV-like behavior with no hysteresis upon desorption (FIG. 3). The material shows a minor step at about a p/po=0.08-0.09 in the $N_2$ isotherm followed by a second step that reaches saturation at approximately 895 cc/g. Using this data, a total pore volume of 1.4 cm$^3$/g has been determined, and the apparent specific surface area is calculated using the Langmuir method and is estimated to be 3800 m$^2$/g. The Ar sorption isotherm is collected on the same sample and shows a similar behavior (FIG. 4). Pore size distribution for UMCM-450b is determined from the Ar isotherm at 87 K and revealed the presence of micropores 10.5-11.5 Å and 12.5-13 Å in diameter, along with a smaller distribution of mesopores 21-23 Å in diameter (FIG. 5).

2. Synthesis of Biphenyl-3,4',5-tricarboxylic acid and UMCM-150

Dimethyl 5-bromoisophthalate is purchased from Matrix Scientific. Palladium tetrakis(triphenylphosphine) is purchased from Pressure Chemical. Methyl 4-carboxyphenylboronic acid is prepared from 4-carboxyphenylboronic acid (Frontier Scientific) according to a published procedure. All other reagents are purchased from Sigma-Aldrich or Acros. All reagents and solvents are used as received.

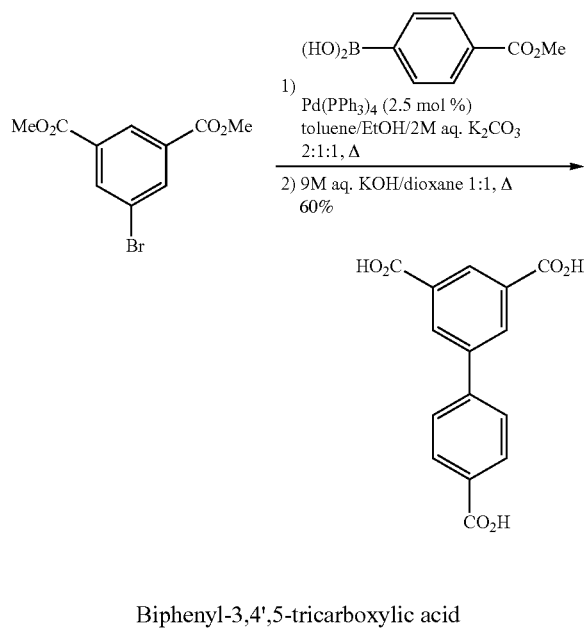

Biphenyl-3,4',5-tricarboxylic acid

Dimethyl 5-bromoisophthalate (8.15 g, 29.9 mmol), methyl 4-carboxyphenylboronic acid (5.91 g, 32.8 mmol), K$_2$CO$_3$ (8.29 g, 60.0 mmol), toluene (60 mL), ethanol (30 mL) and water (30 mL) are added into a 200 mL round-bottomed flask equipped with a magnetic stir bar and water jacketed condenser. The resulting suspension is degassed for 15 min by sparging with nitrogen gas. Pd(PPh$_3$)$_4$ (0.862 g, 0.746 mmol) is added, and the mixture is heated to reflux overnight under a nitrogen atmosphere. After cooling to room temperature both layers are separated, the organic layer is dried over anhydrous Na$_2$SO$_4$, filtered and the solvent is removed under reduced pressure. The residue is filtered on a short silica plug using acetone as eluent and the solvent is removed by evaporation. The crude product is dissolved in dioxane (50 mL) and an aqueous KOH solution (9 M, 50 mL) is added. This mixture is heated to reflux for 12 h. The solvent is evaporated then the residue is dissolved in H$_2$O (100 mL). The residual solids are filtered off and the filtrate is acidified with concentrated HCl (20 mL). The target compound is collected by filtration, washed with H$_2$O and acetone and dried under vacuum to yield 5.15 g of biphenyl-3,4',5-tricarboxylic acid (18.0 mmol as a white powder, 60%): mp>300° C.; $^1$H NMR (400 MHz, DMSO-d$_6$): δ 13.23 (br s, 3H), 8.41 (d, J=1.0 Hz, 1H), 8.33 (t, J=1.0 Hz, 2H), 7.99 (d, J=8.0 Hz, 2H), 7.77 (d, J=8.0 Hz, 2H); $^{13}$C NMR (100 MHz, DMSO-d$_6$): δ 167.4, 166.8, 142.8, 140.3, 132.6, 131.8, 130.8, 130.6, 129.9, 127.4; HRMS (EI) calcd. for C$_{15}$H$_{10}$O$_6$ (m/e): 286.0477. found: 286.0485; Anal. Calcd for C$_{15}$H$_{10}$O$_6$: C, 62.94; H, 3.52. Found: C, 62.54; H, 3.57.

UMCM-150.

Biphenyl-3,4',5-tricarboxylic acid (0.0500 g, 0.175 mmol) and Cu(NO$_3$)$_2$.2.5H$_2$O (0.0980 g, 0.525 mmol) are dissolved in DMF/dioxane/H$_2$O (4:1:1, 15 mL). The solution is placed in a tightly capped 20 mL vial and heated at 85° C. for 6 hours. Upon cooling the mother liquor is removed and replaced twice with fresh DMF and then with acetone. The acetone is replaced with fresh solvent three times over a period of three days. The crystals are then placed in a Schlenk tube and dried under vacuum at ambient temperature until the material started to change color to deep purple. The crystals are further evacuated at 100° C. for 1-2 hours to yield 0.052 g of activated UMCM-150 (0.137 mmol as blue-green crystals, 78% based on fully evacuated material): mp>300° C. (dec); PXRD (Cu Kα, 1.5418 Å) 2θ (I/I$_0$): 4.3 (44%), 6.9 (100%), 8.7 (29%), 10.3 (24%), 10.8 (27%), 11.7 (17%), 14.0 (38%); Anal. Calcd for C$_{15}$H$_7$O$_6$Cu$_{1.5}$: C, 47.59; H, 1.86. Found: C, 47.19; H, 2.07.

Figure 6:
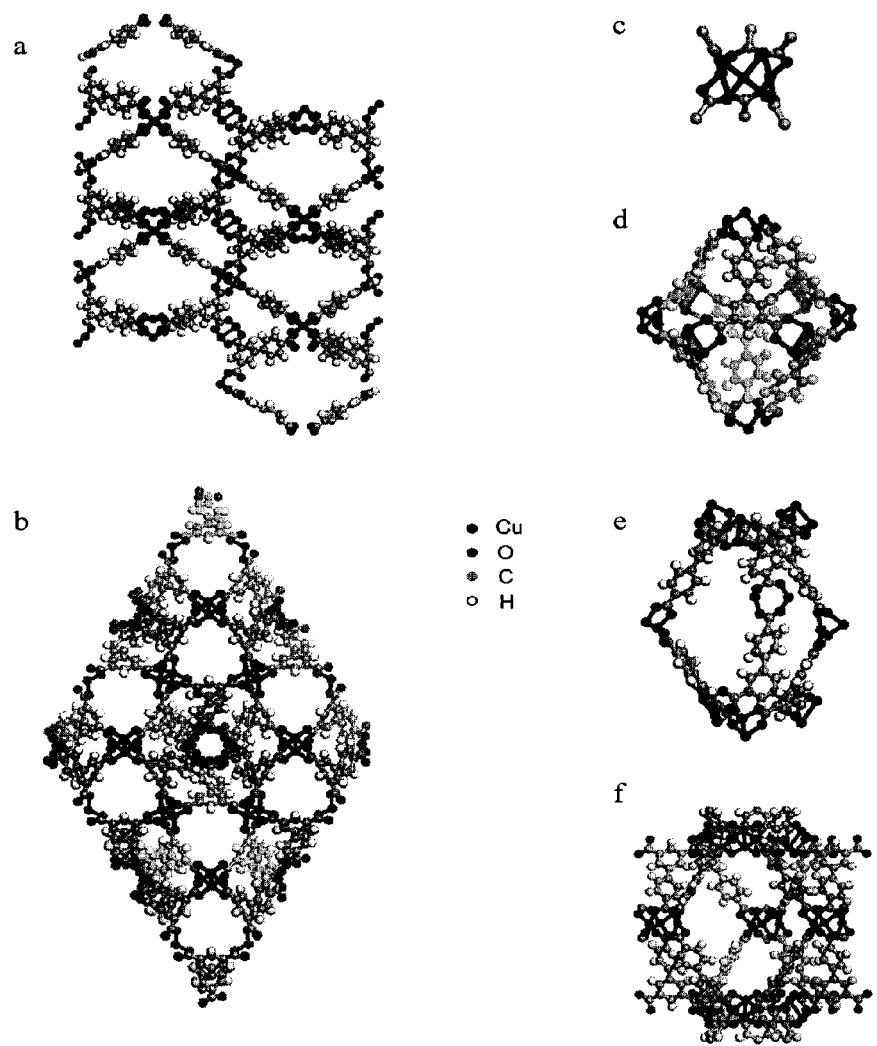
FIG. 6 is a ball and stick drawing illustrating the structure of the network of UMCM-150.

The structure of UMCM-150 is solved by single crystal X-ray diffraction in the space group P63/mmc. Views of the crystal lattice along the a and c axes are provided in FIGS. 6a and 6b. From the X-ray data, the carboxylates on the 3- and 5-positions (same ring) of the linker each form Cu paddlewheel clusters with three neighboring molecules. Notably, the carboxylate on the 4'-position assembles into a Cu$_3$(O$_2$CR)$_6$ cluster (FIG. 6c), UMCM-150 derives from a [3,4,6]-connected net consisting of three types of cage-like structures. One type of cage possesses a hexagonal bipyramidal shape with an aperture (accounting for the van der Waals radii) of approximately 5.2 Å×5.8 Å (FIG. 6d). The walls of the cages are formed by the faces of six linker molecules. Trinuclear Cu clusters are located in the apical positions whereas Cu paddlewheels occupy the equatorial positions. The second type of cage possesses a trigonal bipyramidal shape with a larger aperture of 10.2 Å×13.7 Å. In the apical positions small cylindrical pores about 4.2 Å in diameter resulting from the assembly of three linker molecules by three paddlewheels are observed; Cu$_3$ clusters are located in the equatorial positions and linker molecules occupy the faces (FIG. 6e). The third type of cage possesses all three different apertures observed in the other two types of cages (FIG. 6f). Each apical position of the cage is formed from three paddlewheels and three linker molecules pointing outward, while three Cu$_3$ clusters are located in the equatorial positions. The edges of twelve linker molecules form the cage walls. Notably, for the first two types of cages only aromatic groups face towards the inside, whereas the axial coordination sites of the Cu paddlewheels are directed inward in the third type of cage.

Figure 7:
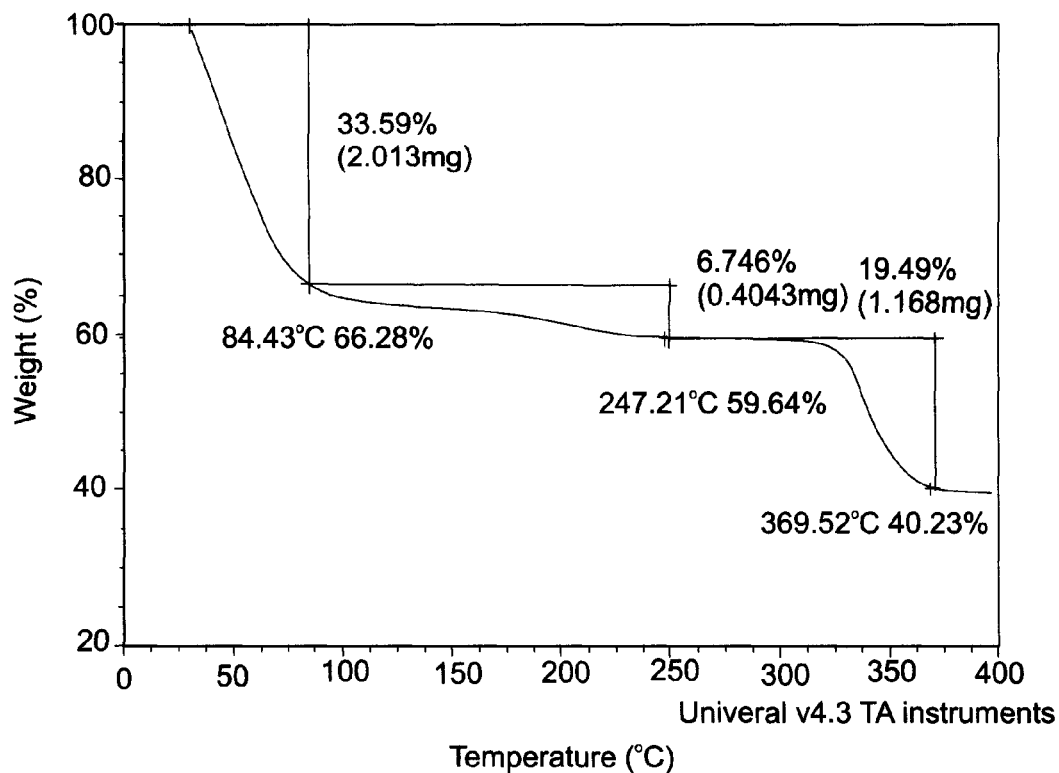
FIG. 7 provides the thermal gravimetric analysis (TGA) of UMCM-150 where the guest solvent has been exchanged with acetone prior to analysis. Percentages of weight loss and the corresponding temperatures are shown.

Thermogravimetric measurements are taken on a TA Q50 TGA apparatus. Samples (typically 5-10 mg) are loaded on a platinum pan, and the temperature is ramped at 5° C./min from 30 to 400° C. Thermogravimetric analysis of this material reveals rapid solvent loss over the temperature range of 25-125° C. reaching a plateau from 125-150° C. A 6.7% weight loss observed from 150-225° C. is attributed to molecules bound to Cu atoms. (FIG. 7). Removal of the solvent from the framework by evacuation at 100° C. for 4 hours leads to a change in color of the material to deep purple. The evacuated material is formulated as Cu$_3$(C$_{15}$H$_7$O$_6$)$_2$ by elemental analysis and this assignment is corroborated by X-ray crystallography (vide infra) No significant change in the PXRD pattern is observed after solvent.

Figure 8:
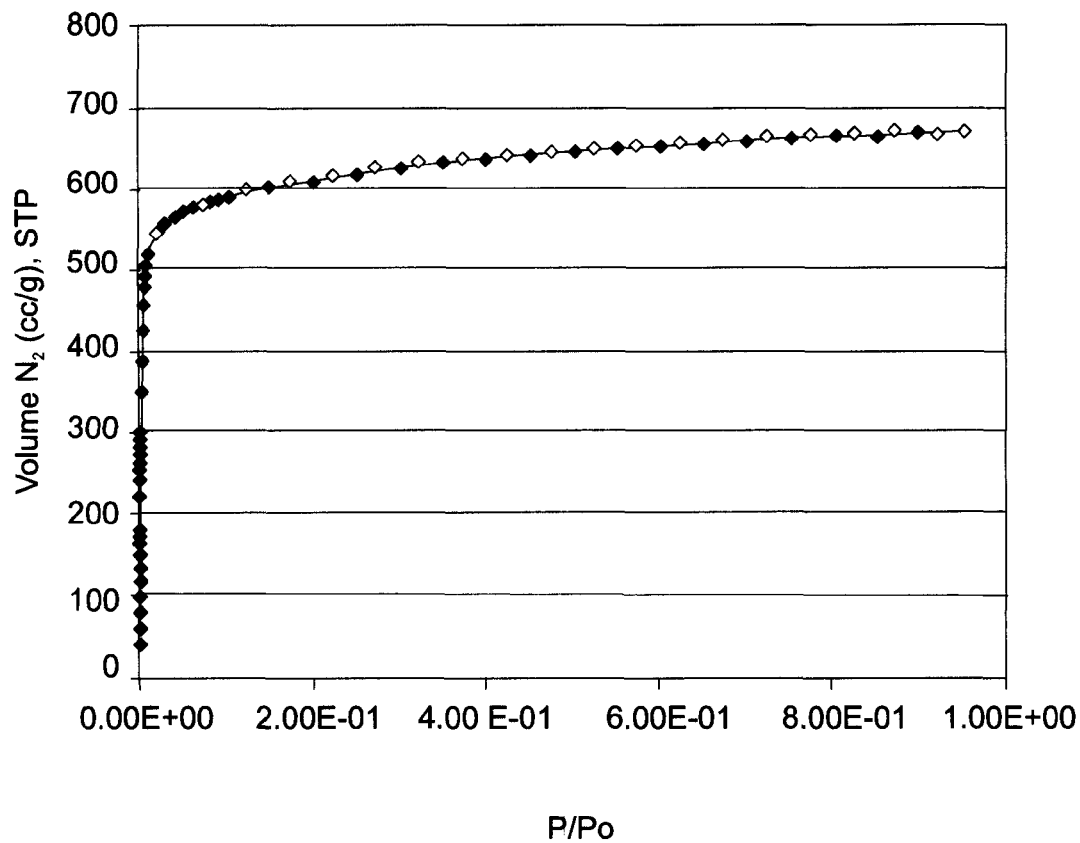
FIG. 8 is a plot of the nitrogen gas sorption isotherm at 77 K for UMCM-150 (filled triangles, adsorption; open triangles, desorption)

N$_2$ adsorption/desorption isotherms are measured volumetrically at 77 K in the range $1.00 \times 10_{-3} \leq P/P_o \leq 1.00$ with an Autosorb-1C outfitted with the micropore option by Quantachrome Instruments (Boynton Beach, Fla. USA), running version 1.2 of the ASWin software package. Ultra-high purity He (99.999%, for void volume determination) and N2 (99.999%) are purchased from Cryogenic Gasses and used as received. The N$_2$ adsorption isotherm (FIG. 8) of UMCM-150 reveals type I behavior with no hysteresis upon desorption. From this data, a total pore volume of 1.0 cm$^3$/g is determined, and the apparent surface area is calculated using the Langmuir method to be 3100 m$^2$/g (2300 m$^2$/g BET), thus confirming the permanent porosity of UMCM-150.

Figure 9:
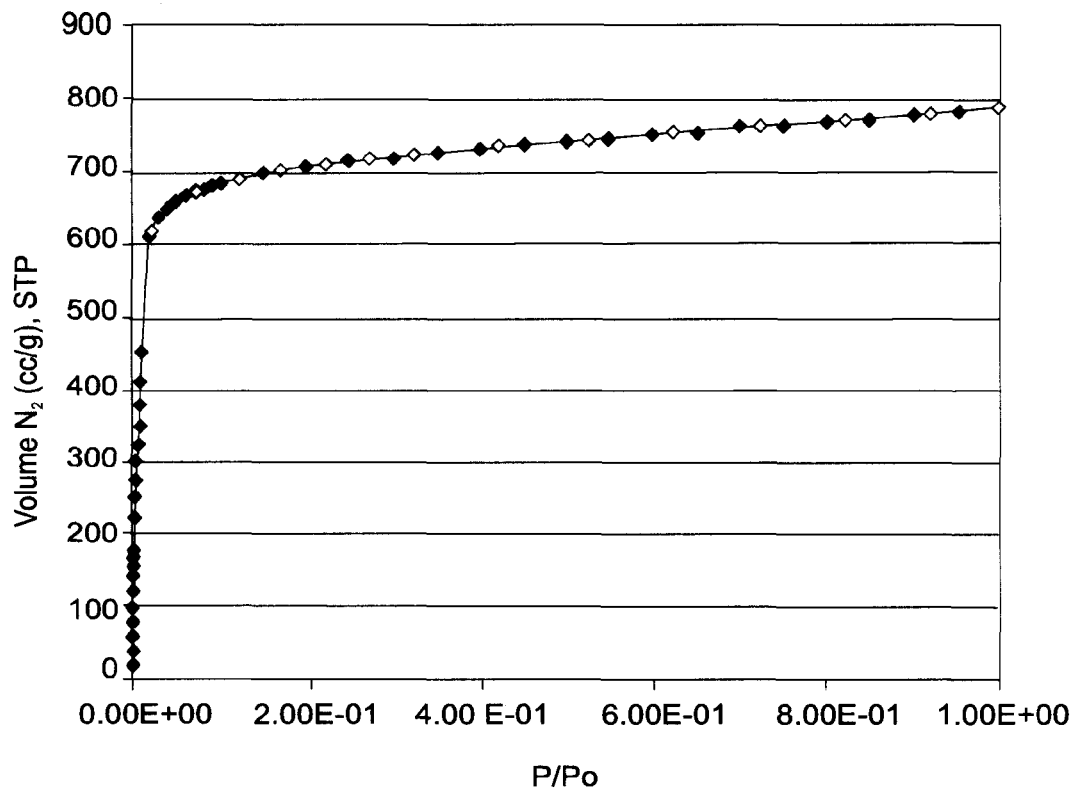
FIG. 9 is a plot of the argon gas sorption isotherm at 87 K for UMCM-450b (filled triangles, adsorption; open triangles, desorption)
Figure 10:
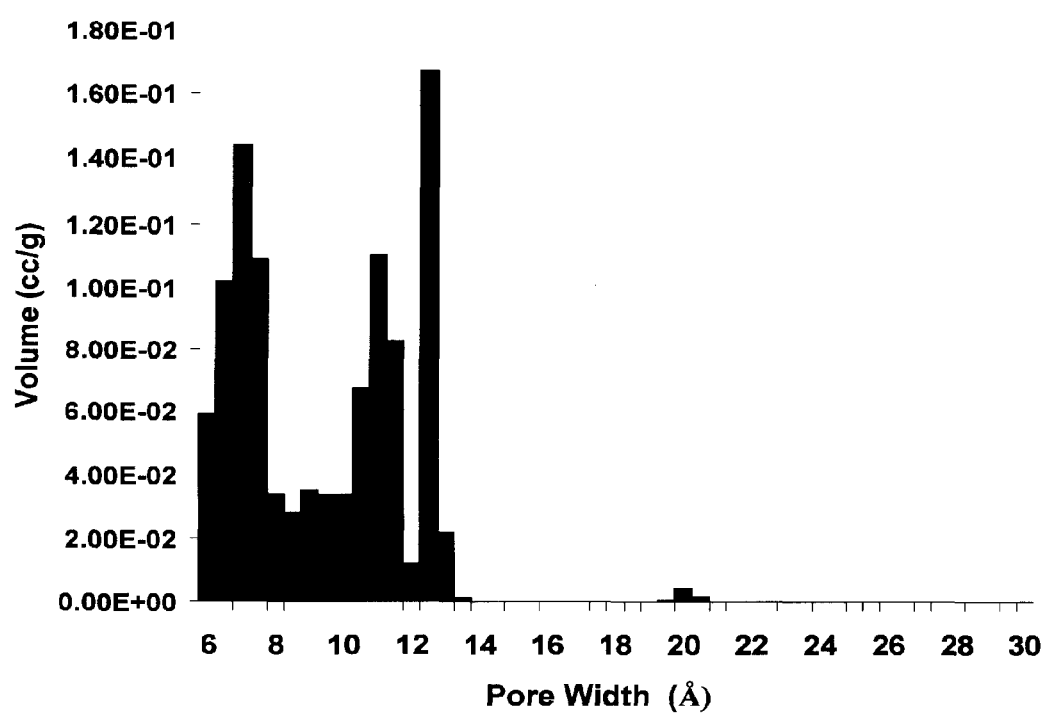
FIG. 10 is a histogram of the pore size distribution for UMCM-450b and Pore size distribution is determined from the argon isotherm at 87 K.

Ar adsorption/desorption isotherms are measured similarly (FIG. 9). Ultra-high purity Ar (99.999%) is purchased from Cryogenic Gasses and used as received. Pore size distributions (FIG. 10) are determined by analyzing the Ar isotherm at 87 K using nonlocal density functional theory (NLDFT) implementing a hybrid kernel for argon adsorption at liquid-argon temperature based on a zeolite/silica model containing cylindrical pores as implemented in the ASW in software package. Ar adsorption yields the following pore distribution diameters: 6.5-8 Å, 10.5-12 Å, and 12.5-13 Å. These pore sizes are consistent with the three types of cages observed in the crystal structure.

Figure 11:
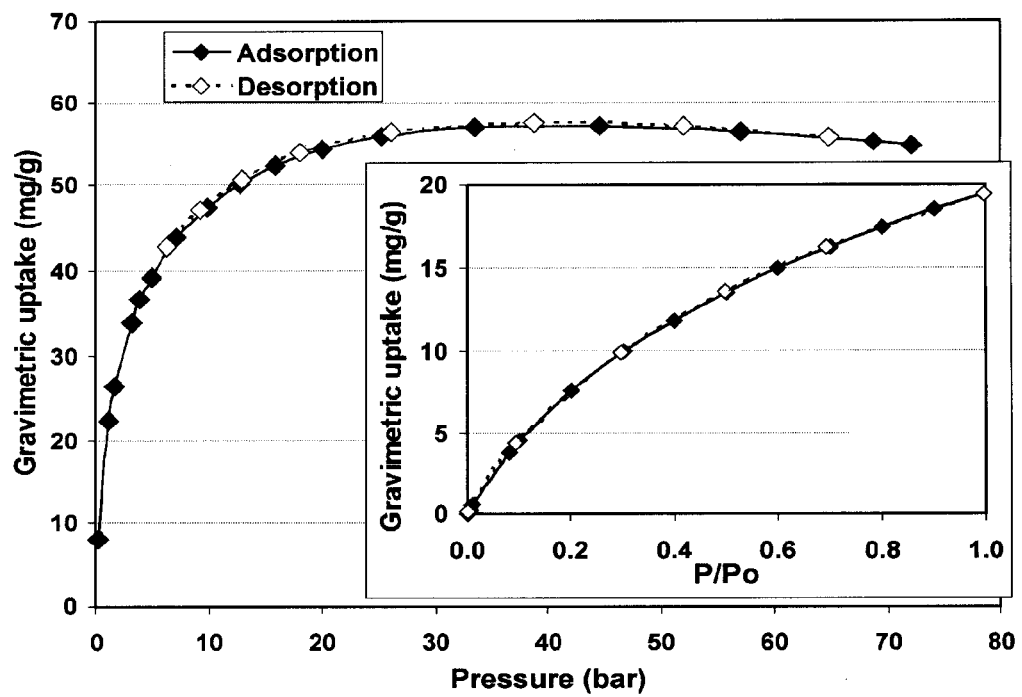
FIG. 11 is a hydrogen sorption isotherm at 77 K for UMCM-150. The inset is an isotherm from 0 to 1 bar.

The H$_2$ adsorption isotherm recorded at 77K shows type I behavior with no hysteresis and no noticeable change in properties upon repeated cycling. UMCM-150 shows an excess gravimetric H$_2$ uptake of 1.9 wt % at 1 bar (FIG. 11), which indicates the presence of high affinity sites. High pressure studies on UMCM-150 revealed 5.7 wt % at 45 bar (FIG. 11). From the crystallographic density of the fully evacuated material (0.636 g/cm$^3$), an upper limit on the excess volumetric uptake could be estimated as 36 g/L. These values are among the highest reported for both excess gravimetric and volumetric H$_2$ uptake by a reversible sorbent.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A coordination polymer defining a molecular framework, the coordination polymer comprising:
   a plurality of metal atoms or metal clusters, and
   a plurality of organic linking ligands, each linking ligand comprising a residue of a compound having Formula I or VII:

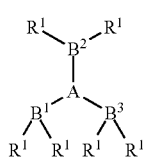

(I)

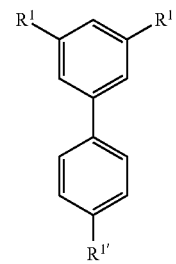

(VII)

wherein:
   $R^1$ and $R^{1'}$ are each independently $CO_2R^2$, $CONR^2_2$, CN, a $C_{2-8}$ alkynyl, or a $C_{4-18}$ heteroatom-containing aromatic ring system;
   $R^2$ is H, a metal cation, an organic cation, $C_{1-8}$ alkyl, $C_{1-8}$ perfluoroalkyl, a $C_{6-18}$ aromatic ring system, or a $C_{4-18}$ heteroatom-containing ring system;
   A is a substituted or unsubstituted $C_{6-18}$ aromatic ring system or a $C_{4-18}$ heteroatom-containing ring system; and
   $B^1$, $B^2$, $B^3$ are each independently a substituted or unsubstituted $C_{6-18}$ aromatic ring system, a $C_{4-18}$ heteroatom-containing ring system, $C_{7-18}$ alkyl aryl, or $C_{5-18}$ alkyl heteroaryl, wherein $B^1$, $B^2$, $B^3$ are distributed about the A moiety.

2. The coordination polymer of claim 1 further comprising at least one non-linking ligand.

3. The coordination polymer of claim 2 wherein the non-linking ligand is selected from the group consisting of $O^{2-}$, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite, and combinations thereof.

4. The coordination polymer of claim 1 further comprising at least one adsorbed species.

5. The coordination polymer of claim 4 wherein the adsorbed species is selected from the group consisting of ammonia, carbon dioxide, carbon monoxide, hydrogen, amines, methane, oxygen, argon, nitrogen, argon, organic dyes, polycyclic organic molecules, and combinations thereof.

6. The coordination polymer of claim 1 wherein the metal clusters comprise a metal ion selected from the group consisting Group 1 through 16 metals of the IUPAC Periodic Table of the Elements including actinides, lanthanides and combinations thereof.

7. The coordination polymer of claim 1 wherein the metal cluster further contains at least one atom from the group consisting of N, P, As, Sb, Bi, O, S, Se, Te, F, Cl, Br, and I.

8. The coordination polymer of claim 1 having described by the following formula $[(C_{48}H_{24}O_{12})Cu_3 \cdot (solvent)_n]_x$ where x is a real number and n is a number from 0 to 50.

9. The coordination polymer of claim 1 further comprising one or more guest molecules occupying space within the framework.

10. The coordination polymer of claim 9 wherein the guest molecules are selected from the group consisting of solvents, gases, amines, organic compounds, coordination compounds, polymers, organic particles, organometallic particles, inorganic particles, and combinations thereof.

11. The coordination polymer of claim 9 wherein the guest molecules are selected from the group consisting of water, small organic alkanes, arenes, ethers, haloalkanes, esters, amides, sulfides, sulfoxides, amines, ketones, aldehydes, alcohols, thiols, hydrogen, ammonia, methane, oxygen, nitrogen, argon, carbon monoxide, carbon dioxide, nitrous oxide, sulfur dioxide, sulfur trioxide, ethylene, acetylene, and combinations thereof.

12. The coordination polymer of claim 1 having formula $[(C_{15}H_7O_6)_2Cu_3.(solvent)_n]_x$ where x is a real number and n is a number from 0 to 50.

13. The coordination polymer of claim 1 wherein each linking ligand comprises a residue of a compound having formula VII:

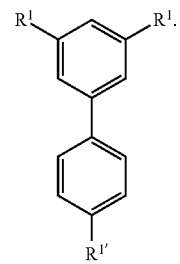

(VII)

14. The coordination polymer of claim 13 wherein $R^1$ and $R^{1'}$ are $CO_2H$.

15. The coordination polymer of claim 13 wherein the center of mass of moiety B is at least 4 angstroms from the center of mass of moiety A.

16. The coordination polymer of claim 13 wherein the center of mass of moiety B is from about 7 to about 25 angstroms from the center of mass of moiety A.

* * * * *